(12) United States Patent
Galun et al.

(10) Patent No.: US 6,217,858 B1
(45) Date of Patent: Apr. 17, 2001

(54) PHARMACEUTICAL COMPOSITION FOR TREATING HEPATITIS B VIRUS (HBV) INFECTION

(75) Inventors: Eithan Galun, Har Adar; Orit Nahor, Jerusalem, both of (IL); Hubert E. Blum, Freiburg (DE)

(73) Assignee: Hadasit & Medical Research Services & Development Company, Ltd., Jerusalem (IL)

( * ) Notice: Subject to any disclaimer, the term of this patent is extended or adjusted under 35 U.S.C. 154(b) by 0 days.

(21) Appl. No.: 08/795,473

(22) Filed: Feb. 11, 1997

(51) Int. Cl.[7] .......................... A61K 45/05; A61K 39/29; A61K 38/20
(52) U.S. Cl. ..................... 424/85.2; 424/89; 424/189.1; 424/225.1; 424/227.1
(58) Field of Search .................................. 424/189.1, 89, 424/84.2, 225.1, 227.1

(56) References Cited

U.S. PATENT DOCUMENTS 5,158,769 * 10/1992 Neurath et al. ..................... 424/89
5,338,833    8/1994 Fowlkes et al. .

FOREIGN PATENT DOCUMENTS

| 0572118 | 1/1993 | (EP) | ............... | C12P/21/08 |
| 2694767 | 2/1994 | (FR) | ............... | C12P/21/08 |
| WO9210570 | 6/1992 | (WO) | ............... | C12N/15/12 |
| WO9617869 | 6/1996 | (WO) | ............... | C07K/14/715 |

OTHER PUBLICATIONS

"Search for Hepatitis B Virus Cell Re Binding Sites for Interleukin 6 on the Envelope Protein", by A. Robert Neurath, et al., The Rockfeller University Press, vol. 175, Feb. 1992, pp. 461–469.

Review Article—"The Recognition event between virus and host cell receptor: a target for antiviral agents", Thomas L. Lentz, Journal of General Virology (1990), 71, pp. 751–766.

"A short cis–acting sequence is required for hepatitis B virus pregenome encapsidation and sufficient for packaging of foreign RNA", The EMBO Journal, vol. 9, No. 10, pp. 3389–3396, 1990.

"The encapsidation signal on the hepatitis B virus RNA pregenome forms a stem–loop structure that is critical for its function", Thomas Knaus et al., 1993 Oxford University Press, Nucleic Acid Research, 1993, vol. 21, No. 17, pp. 3967–3975.

"Naturally Occurring Missense Mutation in the Polymerase Gene Terminating Hepatitis B Virus Replication", Hubert E. Blum, et al., Journal of Virology, Apr. 1991, vol. 65, No. 4, pp. 1836–1842.

Gene transfer in vivo: Sustained expression and regulation of genes introduced into the liver by receptor–targeted uptake, Jose Carlos Perales, et al., Proc. Natl. Acad. Sci. USA, vol. 91, pp. 4086–4090, Apr. 1994, Medical Sciences.

"Delayed Morbidity and Mortality of Albumins/SV40 T–Antigen Transgenic Mice after insertion of an ∂–Feto-protein/Herpes Virus Thymidine Kinase Transgene and Treatment with Ganciclovir", Paola Macri et al., Human Gene Therapy 5:175–182 (1994), Mary Ann Liebert, Inc., Publ.

Neurath et al. (AR) J. Exp. Med. 175: 461–469 Feb. 1992.*
Baroja et al. Viral Immunology 9(3): 187–194, 1996.*
Neurath et al. (B) Vaccine (ENGLAND) 7(3): 234: 236, Jun. 1989.*
P. Pontisso, et al., Gastroenterology, 1983, vol. 84, No. 2, pp. 220–226.
A. Machida, et al., Gastroenterology, 1983, vol. 85, No. 2, pp. 269–274.
Marie–Louise Michel, et al., Biochemistry, Dec. 1984, vol. 81, pp. 7708–7712.
A. Machida, et al., Gastroenterology, 1984, vol. 86, No. 5, pp. 910–918.
P. Pontisso, et al., Journal of Virology, May 1989, pp. 1981–1988.
A.R. Neurath, et al., Cell, 1986, vol. 46, pp. 429–436.
Marie–Anne Petit, et al., Molecular Immunology, vol. 26, No. 6, pp. 531–537.
A. R. Neurath, et al., Virology, 1990, vol. 176, pp. 448–457.
F. D'Mello, et al., Virology, 1997, vol. 237, pp. 319–326.
M. E. Peeples, et al., 1987, vol. 160, pp. 135–142.
K. Komai, et al., Virology, 1990, vol. 177, pp. 332–338.
K. Komai, et al., Virology, 1988, vol. 163, pp. 629–634.
P. Pontisso, et al., Journal of General Virology, 1992, vol. 73, pp. 2041–2045.
S. Dash, et al., All India Institute of Medical Sciences, 1991, vol. 13, No. 1, pp. 134–142.
A. Budkowska, et al., Journal of Virology, 1993, vol. 67, No. 7, pp. 4316–4322.
M.–C. Gagliardi, et al., Eur. J. Immunol., 1994, vol. 24, pp. 1372–1376.
U. Treichel, et al., Journal of General Virology, 1994, vol. 75, pp. 3021–3029.
K. Hertogs, et al., University Hospital Gasthuisberg, 1993, vol. 197, pp. 549–557.

(List continued on next page.)

Primary Examiner—Chris Eisenschenk
Assistant Examiner—Mary K Zeman
(74) Attorney, Agent, or Firm—Davidson, Davidson & Kappel, LLC

(57) ABSTRACT

The invention provides a pharmaceutical composition for the treatment of hepatitis B virus (HBV) infection, comprising an amount of a soluble active agent which interacts with at least one of the binding sites between hIL6 and pS1 and between hIL6 and hepatocytes and other HBV-permissive cells, the active agent being present in sufficient amount to competitively bind to at least one of the sites and thereby to prevent hIL6-mediated HBV infection of hepatocytes and other HBV-permissive cells.

11 Claims, 14 Drawing Sheets

Figure 1:
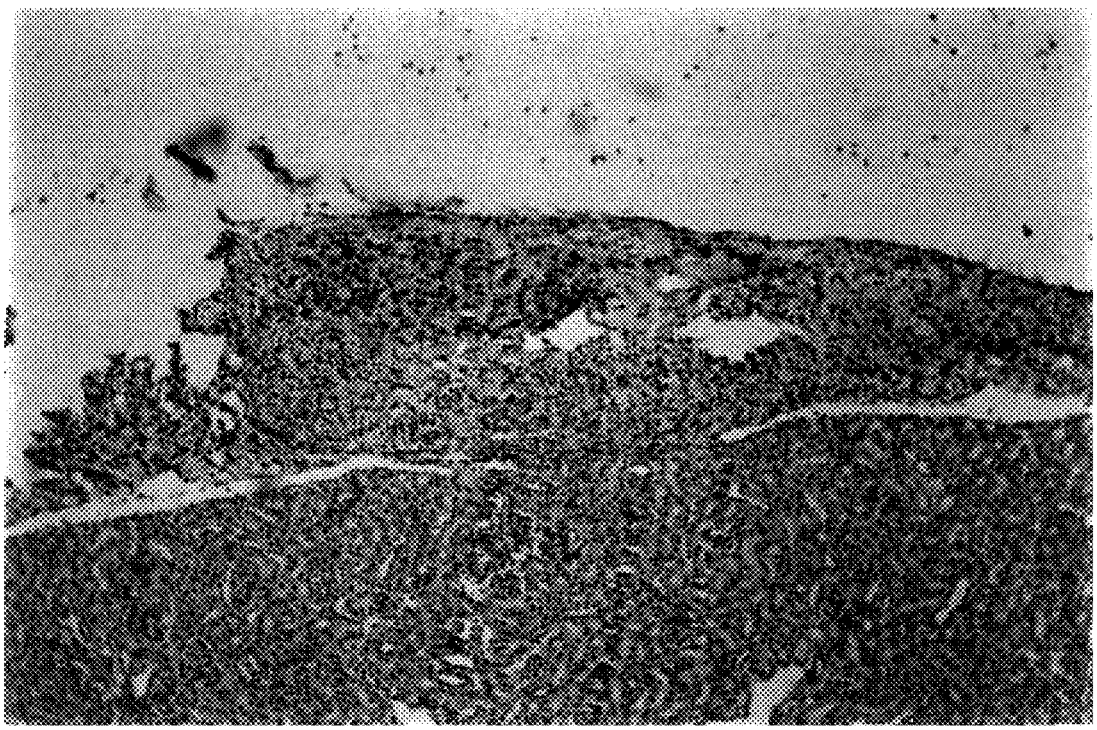

(3 of 14 Drawing Sheet(s) Filed in Color)

OTHER PUBLICATIONS

H. Mehdi, et al., Journal of Virology, 1994, vol. 68, No. 4, pp. 2415–2424.
M–.A. Petit, et al., Virology, 1992, vol. 187, pp. 211–222.
A. Franco, et al., J. Exp. Med. 1992, vol. 175, pp. 1195–1205.
S. Dash, et al., Journal of Medical Virology, 1992, vol. 37, pp. 116–121.
Y. Mizutani, et al., Cancer Research, 1995, vol. 55, pp. 590–596.
J.P.J. Brakenoff, et al., The Journal of Biological Chemistry, 1994, vol. 269, No. 1, pp. 86–93.
M. Peters, et al., J. Exp. Med., 1996, vol. 183, pp. 1399–1406.
M. Peters, et al., Immunology Letters, 1996, vol. 54, pp. 177–184.
E. Sporeno, et al., Blood, 1996, vol. 87, No. 11, pp. 4510–4519.
R. Masood, et al., Aids Research and Human Retroviruses, 1994, vol. 10, pp. 969–970.
W. Somers, et al., The EMBO Journal, 1997, vol. 16, No. 5, pp. 989–997.
A. Neurath, et al. J. Exp. Med., 1992, vol. 176, pp. 1561–1569.
Abstract: Medline 96134845 (Nishimura, Biochemistry 35:273–281 (1996).
Abstract: Medline 91084844 (Hibi, Cell 63(6):1149–1157 (1990).
Abstract:Medline 87067433 (May, Proc. Nat'l Acad. Sci. U.S.A. 8323):8957–8961(1986).
Abstact:Medline 91336983 (schooltink, Biochem.J. 277:659–664(1991).
Abstract: Medline 88305347 and 91336983 (Yamasaki, Science 241:825–828 (1988)), 5 pages.
R. Savino, et al., "Generation of interleukin–6 receptor antagonists by . . . activation", The EMBO Journal, vol. 13, No. 6, pp. 1357–1367, (1994).
R. Neurath, et al., "Cells Transfected with Human Interleukin 6 cDNA Acquire Binding Sites for the Hepatitis B Virus Envelope Protein", J. Exp. Med., The Rockfeller University Press, vol. 176, pp. 1561–1569. (Dec. 1992).
F. Martin, et al., The EMBO Journal, 1994, vol. 13, No. 22, pp. 5303–5309.
Abstract of Japanese Patent No. 02188660, Koishihara et al., July 24, 1990, "Preparation of Peptide Human B–Cell Stimulating Factor 2(BSF2) Antagonists".

* cited by examiner

FIG.2A
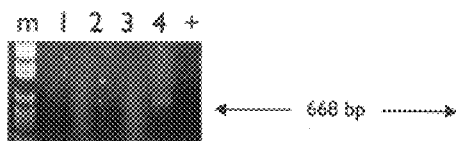
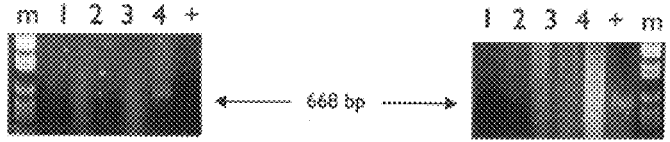
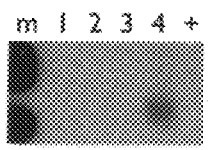
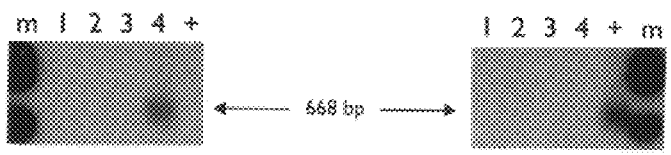
FIG.2B
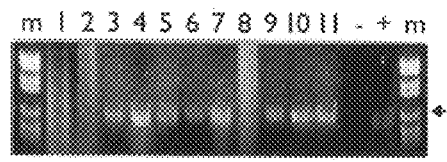
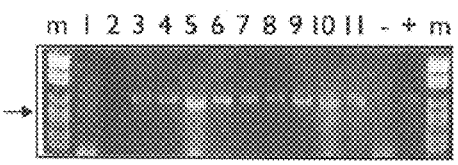
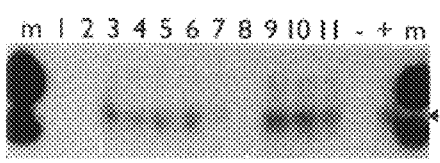
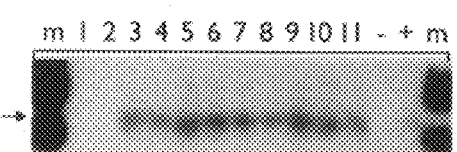

FIG.2C
d 16
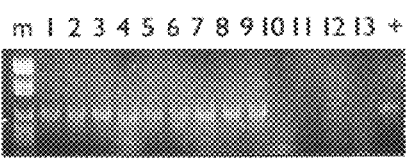
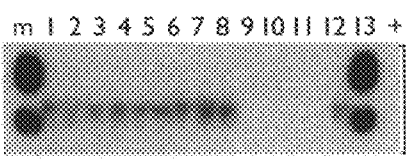
d 31
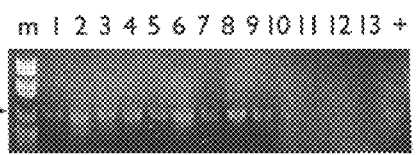
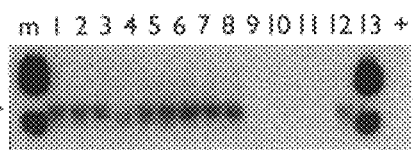
←—668 bp—→

```
ATTCTGCCCT CGAGCCCACC GGGAACGAAA GAGAAGCTCT ATCTCCCTC    50
CAGGAGCCCA GCTATGAACT CCTTCTCCAC AAGCGCCTTC GGTCCAGTTG  100
CCTTCTCCCT GGGGCTGCTC CTGGTGTTGC CTGCTGCCTT CCCTGCCCCA  150
GTACCCCCAG GAGAAGATTC CAAAGATGTA GCCGCCCCAC ACAGACAGCC  200
ACTCACCTCT TCAGAACGAA TTGACAAACA AATTCGGTAC ATCCTCGACG  250
GCATCTCAGC CCTGAGAAAG GAGACATGTA ACAAGAGTAA CATGTGTGAA  300
AGCAGCAAAG AGGCACTGGC AGAAAACAAC CTGAACCTTC CAAAGATGGC  350
TGAAAAAGAT GGATGCTTCC AATCTGGATT CAATGAGGAG ACTTGCCTGG  400
TGAAAATCAT CACTGGTCTT TTGGAGTTTG AGGTATACCT AGAGTACCTC  450
CAGAACAGAT TTGAGAGTAG TGAGGAACAA GCCAGAGCTG TCCAGATGAG  500
TACAAAAGTC CTGATCCAGT TCCTGCAGAA AAAGGCAAAG AATCTAGATG  550
CAATAACCAC CCCTGACCCA ACCACAAATG CCAGCCTGCT GACGAAGCTG  600
CAGGCACAGA ACCAGTGGCT GCAGGACATG ACAACTCATC TCATTCTGCG  650
CAGCTTTAAG GAGTTCCTGC AGTCCAGCCT GAGGGCTCTT CGGCAAATGT  700
AGCATGGGCA CCTCAGATTG TTGTTGTTAA TGGGCATTCC TTCTTCTGGT  750
CAGAAACCTG TCCACTGGGC ACAGAACTTA TGTTGTTCTC TATGGAGAAC  800
TAAAAGTATG AGCGTTAGGA CACTATTTTA ATTATTTTA  ATTTATTAAT  850
ATTTAAATAT GTGAAGCTGA GTTAATTTAT GTAAGTCATA TTTTATATTT  900
TTAAGAAGTA CCACTTGAAA CATTTATGT  ATTAGTTTTG AAATAATAAT  950
GGAAAGTGGC TATGCAGTTT GAATATCCTT TGTTTCAGAG CCAGATCATT 1000
TCTTGGAAAG TGTAGGCTTA CCTCAAATAA ATGGCTAACT TTATACATAT 1050
TTTTAAAGAA ATATTTATAT TGTATTTATA TAATGTATAA ATGGTTTTTA 1100
TACCAATAAA TGGCATTTTA AAAAATTC                         1128
```

*FIG. 4*

```
GGCGGTCCCC TGTTCTCCCC GCTCAGGTGC GGCGCTGTGG CAGGAAGCCA   50
CCCCCTCGGT CGGCCGGTGC GCGGGGCTGT TGCGCCATCC GCTCCGGCTT  100
TCGTAACCGC ACCCTGGGAC GGCCCAGAGA CGCTCCAGCG CGAGTTCCTC  150
AAATGTTTTC CTGCGTTGCC AGGACCGTCC GCCGCTCTGA GTCATGTGCG  200
AGTGGGAAGT CGCACTGACA CTGAGCCGGG CCAGAGGGAG AGGAGCCGAG  250
CGCGGCGCGG GGCCGAGGGA CTCGCAGTGT GTGTAGAGAG CCGGGCTCCT  300
GCGGATGGGG GCTGCCCCG GGGCCTGAGC CGCCTGCCC GCCCACCGCC   350
CCGCCCCGCC CCTGCCACCC CTGCCGCCCG GTTCCCATTA GCCTGTCCGC  400
CTCTGCGGGA CCATGGAGTG GTAGCCGAGG AGGAAGCATG CTGGCCGTCG  450
GCTGCGCGCT GCTGGCTGCC CTGCTGGCCG CGCCGGGAGC GGCGCTGGCC  500
CCAAGGCGCT GCCCTGCGCA GGAGGTGGCA AGAGGCGTGC TGACCAGTCT  550
GCCAGGAGAC AGCGTGACTC TGACCTGCCC GGGGGTAGAG CCGGAAGACA  600
ATGCCACTGT TCACTGGGTG CTCAGGAAGC CGGCTGCAGG CTCCCACCCC  650
AGCAGATGGG CTGGCATGGG AAGGAGGCTG CTGCTGAGGT CGGTGCAGCT  700
CCACGACTCT GGAAACTATT CATGCTACCG GGCCGGCCGC CCAGCTGGGA  750
CTGTGCACTT GCTGGTGGAT GTTCCCCCCG AGGAGCCCCA GCTCTCCTGC  800
TTCCGGAAGA GCCCCCTCAG CAATGTTGTT TGTGAGTGGG GTCCTCGGAG  850
CACCCCATCC CTGACGACAA AGGCTGTGCT CTTGGTGAGG AAGTTTCAGA  900
ACAGTCCGGC CGAAGACTTC CAGGAGCCGT GCCAGTATTC CAGGAGTCC   950
CAGAAGTTCT CCTGCCAGTT AGCAGTCCCG GAGGGAGACA GCTCTTTCTA 1000
CATAGTGTCC ATGTGCGTCG CCAGTAGTGT CGGGAGCAAG TTCAGCAAAA 1050
CTCAAACCTT TCAGGGTTGT GGAATCTTGC AGCCTGATCC GCCTGCCAAC 1100
ATCACAGTCA CTGCCGTGGC CAGAAACCCC CGCTGGCTCA GTGTCACCTG 1150
```

*FIG. 5A*

FIG.5B

```
GCAAGACCCC CACTCCTGGA ACTCATCTTT CTACAGACTA CGGTTTGAGC 1200
TCAGATATCG GGCTGAACGG TCAAAGACAT TCACAACATG GATGGTCAAG 1250
GACCTCCAGC ATCACTGTGT CATCCACGAC GCCTGGAGCG GCCTGAGGCA 1300
CGTGGTGCAG CTTCGTGCCC AGGAGGAGTT CGGGCAAGGC GAGTGGAGCG 1350
AGTGGAGCCC GGAGGCCATG GGCACGCCTT GGACAGAATC CAGGAGTCCT 1400
CCAGCTGAGA ACGAGGTGTC CACCCCATG CAGGCACTTA CTACTAATAA 1450
AGACGATGAT AATATTCTCT TCAGAGATTC TGCAAATGCG ACAAGCCTCC 1500
CAGTGCAAGA TTCTTCTTCA GTACCACTGC CCACATTCCT GGTTGCTGGA 1550
GGGAGCCTGG CCTTCGGAAC GCTCCTCTGC ATTGCCATTG TTCTGAGGTT 1600
CAAGAAGACG TGGAAGCTGC GGGCTCTGAA GGAAGGCAAG ACAAGCATGC 1650
ATCCGCCGTA CTCTTTGGGG CAGCTGGTCC CGGAGAGGCC TCGACCCACC 1700
CCAGTGCTTG TTCCTCTCAT CTCCCCACCG GTGTCCCCCA GCAGCCTGGG 1750
GTCTGACAAT ACCTCGAGCC ACAACCGACC AGATGCCAGG GACCCACGGA 1800
GCCCTTATGA CATCAGCAAT ACAGACTACT TCTTCCCCAG ATAGCTGGCT 1850
GGGTGGCACC AGCAGCCTGG ACCTGTGGA TGACAAAACA CAAACGGGCT 1900
CAGCAAAAGA TGCTTCTCAC TGCCATGCCA GCTTATCTCA GGGGTGTGCG 1950
GCCTTTGGCT TCACGGAAGA GCCTTGCGGA AGGTTCTACG CCAGGGGAAA 2000
ATCAGCCTGC TCCAGCTGTT CAGCTGGTTG AGGTTTCAAA CCTCCCTTTC 2050
CAAATGCCCA GCTTAAAGGG GTTAGAGTGA ACTTGGGCCA CTGTGAAGAG 2100
AACCATATCA AGACTCTTTG GACACTCACA CGGACACTCA AAAGCTGGGC 2150
AGGTTGGTGG GGGCCTCGGT GTGGAGAAGC GGCTGGCAGC CCACCCCTCA 2200
ACACCTCTGC ACAAGCTGCA CCCTCAGGCA GGTGGGATGG ATTTCCAGCC 2250
AAAGCCTCCT CCAGCCGCCA TGCTCCTGGC CCACTGCATC GTTTCATCTT 2300
CCAACTCAAA CTCTTAAAAC CCAAGTGCCC TTAGCAAATT CTGTTTTTCT 2350
AGGCCTGGGG ACGGCTTTTA CTTAAACGCC AAGGCCTGGG GAAGAAGCT 2400
CTCTCCTCCC TTTCTTCCCT ACAGTTCAAA AACAGCTGAG GGTGAGTGGG 2450
TGAATAATAC AGTATGTCAG GGCCTGGTCG TTTTCAACAG AATTATAATT 2500
AGTTCCTCAT TAGCAGTTTT GCCTAAATGT GAATGATGAT CCTAGGCATT 2550
TGCTGAATAC AGAGGCAACT GCATTGGCTT TGGGTTGCAG GACCTCAGGT 2600
GAGAAGCAGA GGAAGGAGAG GAGAGGGGCA CAGGGTCTCT ACCATCCCCT 2650
GTAGAGTGGG AGCTGAGTGG GGGATCACAG CCTCTGAAAA CCAATGTTCT 2700
CTCTTCTCCA CCTCCCACAA AGGAGAGCTA GCAGCAGGGA GGGCTTCTGC 2750
CATTTCTGAG ATCAAAACGG TTTTACTGCA GCTTTGTTTG TTGTCAGCTG 2800
AACCTGGGTA ACTAGGGAAG ATAATATTAA GGAAGACAAT GTGAAAAGAA 2850
AAATGAGCCT GGCAAGAATG CGTTTAAACT TGGTTTTTAA AAAACTGCTG 2900
ACTGTTTTCT CTTGAGAGGG TGGAATATCC AATATTCGCT GTGTCAGCAT 2950
AGAAGTAACT TACTTAGGTG TGGGGAAGC ACCATAACTT TGTTTAGCCC 3000
AAAACCAAGT CAAGTGAAAA AGGAGGAAGA GAAAAAATAT TTTCCTGCCA 3050
GGCATGGAGG CCCACGCACT TCGGGAGGTC GAGGCAGGAG GATCACTTGA 3100
GTCCAGAAGT TTGAGATCAG CCTGGGCAAT GTGATAAAAC CCCATCTCTA 3150
CAAAAAGCAT AAAAATTAGC CAAGTGTGGT AGAGTGTGCC TGAAGTCCCA 3200
GATACTTGGG GGGCTGAGGT GGGAGGATCT CTTGAGCCTG GGAGGTCAAG 3250
GCTGCAGTGA GCCGAGATTG CACCACTGCA CTCCAGCCTG GGGTGACAGA 3300
GCAAGTGAGA CCCTGTCTC                                    3319
```

```
ATTAGCCTGT CCGCCTCTGC GGGACCATGG AGTGGTAGCC GAGGAGGAAG   50
CATGCTGGCC GTCGGCTGCG CGCTGCTGGC TGCCCTGCTG GCCGCGCCGG  100
GAGCGGCGCT GGCCCCAAGG CGCTGCCCTG CGCAGGAGGT GGCGAGAGGC  150
GTGCTGACCA GTCTGCCAGG AGACAGCGTG ACTCTGACCT GCCCGGGGGT  200
AGAGCCGGAA GACAATGCCA CTGTTCACTG GGTGCTCAGG AAGCCGGCTG  250
CAGGCTCCCA CCCCAGCAGA TGGGCTGGCA TGGGAAGGAG GCTGCTGCTG  300
AGGTCGGTGC AGCTCCACGA CTCTGGAAAC TATTCATGCT ACCGGGCCGG  350
CCGCCCAGCT GGGACTGTGC ACTTGCTGGT GGATGTTCCC CCCGAGGAGC  400
CCCAGCTCTC CTGCTTCCGG AAGAGCCCCC TCAGCAATGT TGTTTGTGAG  450
TGGGGTCCTC GGAGCACCCC ATCCCTGACG ACAAAGGCTG TGCTCTTGGT  500
GAGGAAGTTT CAGAACAGTC CGGCCGAAGA CTTCCAGGAG CCGTGCCAGT  550
ATTCCCAGGA GTCCCAGAAG TTCTCCTGCC AGTTAGCAGT CCCGGAGGGA  600
GACAGCTCTT TCTACATAGT GTCCATGTGC GTCGCCAGTA GTGTCGGGAG  650
CAAGTTCAGC AAAACTCAAA CCTTTCAGGG TTGTGGAATC TTGCAGCCTG  700
ATCCGCCTGC CAACATCACA GTCACTGCCG TGGCCAGAAA CCCCCGCTGG  750
CTCAGTGTCA CCTGGCAAGA CCCCCACTCC TGGAACTCAT CTTTCTACAG  800
ACTACGGTTT GAGCTCAGAT ATCGGGCTGA ACGGTCAAAG ACATTCACAA  850
CATGGATGGT CAAGGACCTC CAGCATCACT GTGTCATCCA CGACGCCTGG  900
AGCGGCCTGA GGCACGTGGT GCAGCTTCGT GCCCAGGAGG AGTTCGGGCA  950
AGGCGAGTGG AGCGAGTGGA GCCCGGAGGC CATGGGCACG CCTTGGACAG 1000
AATCCAGGAG TCCTCCAGCT GAGAACGAGG TGTCCACCCC CATGCAGGCA 1050
CTTACTACTA ATAAAGACGA TGATAATATT CTCTTCAGAG ATTCTGCAAA 1100
TGCGACAAGC CTCCCAGTGC AAGATTCTTC TTCAGTACCA CTGCCCACAT 1150
TCCTGGTTGC TGGAGGGAGC CTGGCCTTCG GAACGCTCCT CTGCATTGCC 1200
ATTGTTCTGA GGTTCAAGAA GACGTGGAAG CTGCGGGCTC TGAAGGAAGG 1250
CAAGACAAGC ATGCATCCGC CGTACTCTTT GGGGCAGCTG GTCCCGGAGA 1300
GGCCTCGACC CACCCCAGTG CTTGTTCCTC TCATCTCCCC ACCGGTGTCC 1350
CCCAGCAGCC TGGGGTCTGA CAATACCTCG AGCCACAACC GACCAGATGC 1400
CAGGGACCCA CGGAGCCCTT ATGACATCAG CAATACAGAC TACTTCTTCC 1450
CCAGATAGCT GGCTGGGTGG CACCAGCAGC CTGGAC               1486
```

FIG. 6

```
GAGCAGCCAA AAGGCCCGCG GAGTCGCGCT GGGCCGCCCC GGCGCAGCTG    50
AACCGGGGGC CGCGCCTGCC AGGCCGACGG GTCTGGCCCA GCCTGGCGCC   100
AAGGGGTTCG TGCGCTGTGG AGACGCGGAG GGTCGAGGCG GCGCGGCCTG   150
AGTGAAACCC AATGGAAAAA GCATGACATT TAGAAGTAGA AGACTTAGCT   200
TCAAATCCCT ACTCCTTCAC TTACTAATTT TGTGATTTGG AAATATCCGC   250
GCAAGATGTT GACGTTGCAG ACTTGGGTAG TGCAAGCCTT GTTTATTTTC   300
CTCACCACTG AATCTACAGG TGAACTTCTA GATCCATGTG GTTATATCAG   350
TCCTGAATCT CCAGTTGTAC AACTTCATTC TAATTTCACT GCAGTTTGTG   400
TGCTAAAGGA AAAATGTATG GATTATTTTC ATGTAAATGC TAATTACATT   450
GTCTGGAAAA CAAACCATTT TACTATTCCT AAGGAGCAAT ATACTATCAT   500
AAACAGAACA GCATCCAGTG TCACCTTTAC AGATATAGCT TCATTAAATA   550
TTCAGCTCAC TTGCAACATT CTTACATTCG GACAGCTTGA ACAGAATGTT   600
```

FIG. 7A

FIG.7B

```
TATGGAATCA CAATAATTTC AGGCTTGCCT CCAGAAAAAC CTAAAAATTT   650
GAGTTGCATT GTGAACGAGG GGAAGAAAAT GAGGTGTGAG TGGGATGGTG   700
GAAGGGAAAC ACACTTGGAG ACAAACTTCA CTTTAAAATC TGAATGGGCA   750
ACACACAAGT TTGCTGATTG CAAAGCAAAA CGTGACACCC CCACCTCATG   800
CACTGTTGAT TATTCTACTG TGTATTTTGT CAACATTGAA GTCTGGGTAG   850
AAGCAGAGAA TGCCCTTGGG AAGGTTACAT CAGATCATAT CAATTTTGAT   900
CCTGTATATA AAGTGAAGCC CAATCCGCCA CATAATTTAT CAGTGATCAA   950
CTCAGAGGAA CTGTCTAGTA TCTTAAAATT GACATGGACC AACCCAAGTA  1000
TTAAGAGTGT TATAATACTA AAATATAACA TTCAATATAG GACCAAAGAT  1050
GCCTCAACTT GGAGCCAGAT TCCTCCTGAA GACACAGCAT CCACCCGATC  1100
TTCATTCACT GTCCAAGACC TTAAACCTTT TACAGAATAT GTGTTAGGA   1150
TTCGCTGTAT GAAGGAAGAT GGTAAGGGAT ACTGGAGTGA CTGGAGTGAA  1200
GAAGCAAGTG GGATCACCTA TGAAGATAGA CCATCTAAAG CACCAAGTTT  1250
CTGGTATAAA ATAGATCCAT CCCATACTCA AGGCTACAGA ACTGTACAAC  1300
TCGTGTGGAA GACATTGCCT CCTTTTGAAG CCAATGGAAA AATCTTGGAT  1350
TATGAAGTGA CTCTCACAAG ATGGAAATCA CATTTACAAA ATTACACAGT  1400
TAATGCCACA AAACTGACAG TAAATCTCAC AAATGATCGC TATCTAGCAA  1450
CCCTAACAGT AAGAAATCTT GTTGGCAAAT CAGATGCAGC TGTTTTAACT  1500
ATCCCTGCCT GTGACTTTCA AGCTACTCAC CCTGTAATGG ATCTTAAAGC  1550
ATTCCCCAAA GATAACATGC TTTGGGTGGA ATGGACTACT CCAAGGGAAT  1600
CTGTAAAGAA ATATATACTT GAGTGGTGTG TGTTATCAGA TAAAGCACCC  1650
TGTATCACAG ACTGGCAACA AGAAGATGGT ACCGTGCATC GCACCTATTT  1700
AAGAGGGAAC TTAGCAGAGA GCAAATGCTA TTTGATAACA GTTACTCCAG  1750
TATATGCTGA TGGACCAGGA AGCCCTGAAT CCATAAAGGC ATACCTTAAA  1800
CAAGCTCCAC CTTCCAAAGG ACCTACTGTT CGGACAAAAA AAGTAGGGAA  1850
AAACGAAGCT GTCTTAGAGT GGGACCAACT TCCTGTTGAT GTTCAGAATG  1900
GATTTATCAG AAATTATACT ATATTTATA GAACCATCAT TGGAAATGAA  1950
ACTGCTGTGA ATGTGGATTC TTCCCACACA GAATATACAT TGTCCTCTTT  2000
GACTAGTGAC ACATTGTACA TGGTACGAAT GGCAGCATAC ACAGATGAAG  2050
GTGGGAAGGA TGGTCCAGAA TTCACTTTTA CTACCCCAAA GTTTGCTCAA  2100
GGAGAAATTG AAGCCATAGT CGTGCCTGTT TGCTTAGCAT TCCTATTGAC  2150
AACTCTTCTG GGAGTGCTGT TCTGCTTTAA TAAGCGAGAC CTAATTAAAA  2200
AACACATCTG GCCTAATGTT CCAGATCCTT CAAAGAGTCA TATTGCCCAG  2250
TGGTCACCTC ACACTCCTCC AAGGCACAAT TTTAATTCAA AAGATCAAAT  2300
GTATCCAGAT GGCAATTTCA CTGATGTAAG TGTTGTGGAA ATAGAAGCAA  2350
ATGACAAAAA GCCTTTTCCA GAAGATCTGA AATCATTGGA CCTGTTCAAA  2400
AAGGAAAAAA TTAATACTGA AGGACACAGC AGTGGTATTG GGGGTCTTC   2450
ATGCATGTCA TCTTCTAGGC CAAGCATTTC TAGCAGTGAT GAAAATGAAT  2500
CTTCACAAAA CACTTCGAGC ACTGTCCAGT ATTCTACCGT GGTACACAGT  2550
GGCTACAGAC ACCAAGTTCC GTCAGTCCAA GTCTTCTCAA GATCCGAGTC  2600
TACCCAGCCC TTGTTAGATT CAGAGGAGCG GCCAGAAGAT CTACAATTAG  2650
TAGATCATGT AGATGGCGGT GATGGTATTT TGCCCAGGCA ACAGTACTTC  2700
AAACAGAACT GCAGTCAGCA TGAATCCAGT CCAGATATTT CACATTTGA   2750
AAGGTCAAAG CAAGTTTCAT CAGTCAATGA GGAAGATTTT GTTAGACTTA  2800
AACAGCAGAT TTCAGATCAT ATTTCACAAT CCTGTGGATC TGGGCAAATG  2850
AAAATGTTTC AGGAAGTTTC TGCAGCAGAT GCTTTTGGTC CAGGTACTGA  2900
GGGACAAGTA GAAAGATTTG AAACAGTTGG CATGGAGGCT GCGACTGATG  2950
AAGGCATGCC TAAAAGTTAC TTACCACAGA CTGTACGGCA AGGCGGCTAC  3000
ATGCCTCAGT GAAGGACTAG TAGTTCCTGC TACAACTTCA GCAGTACCTA  3050
TAAAGTAAAG CTAAAATGAT TTTATCTGTG AATTC                 3085
```

FIG.8A

|   |   |   |   |   |   |   |   |   |   |   |   |   |   |   |
|---|---|---|---|---|---|---|---|---|---|---|---|---|---|---|
| Met | Leu | Ala | Val | Gly | Cys | Ala | Leu | Leu | Ala | Ala | Leu | Leu | Ala | Ala | Pro |
|     |     |     |     | 5   |     |     |     |     | 10  |     |     |     |     | 15  |     |
| Gly | Ala | Ala | Leu | Ala | Pro | Arg | Arg | Cys | Pro | Ala | Gln | Glu | Val | Ala | Arg |
|     |     |     | 20  |     |     |     |     | 25  |     |     |     |     | 30  |     |     |
| Gly | Val | Leu | Thr | Ser | Leu | Pro | Gly | Asp | Ser | Val | Thr | Leu | Thr | Cys | Pro |
|     |     | 35  |     |     |     |     | 40  |     |     |     |     | 45  |     |     |     |
| Gly | Val | Glu | Pro | Glu | Asp | Asn | Ala | Thr | Val | His | Trp | Val | Leu | Arg | Lys |
|     | 50  |     |     |     |     | 55  |     |     |     |     | 60  |     |     |     |     |
| Pro | Ala | Ala | Gly | Ser | His | Pro | Ser | Arg | Trp | Ala | Gly | Met | Gly | Arg | Arg |
| 65  |     |     |     |     | 70  |     |     |     |     | 75  |     |     |     |     | 80  |
| Leu | Leu | Leu | Arg | Ser | Val | Gln | Leu | His | Asp | Ser | Gly | Asn | Tyr | Ser | Cys |
|     |     |     |     | 85  |     |     |     |     | 90  |     |     |     |     | 95  |     |
| Tyr | Arg | Ala | Gly | Arg | Pro | Ala | Gly | Thr | Val | His | Leu | Leu | Val | Asp | Val |
|     |     |     | 100 |     |     |     |     | 105 |     |     |     |     | 110 |     |     |
| Pro | Pro | Glu | Glu | Pro | Gln | Leu | Ser | Cys | Phe | Arg | Lys | Ser | Pro | Leu | Ser |
|     |     |     | 115 |     |     |     |     | 120 |     |     |     |     | 125 |     |     |
| Asn | Val | Val | Cys | Glu | Trp | Gly | Pro | Arg | Ser | Thr | Pro | Ser | Leu | Thr | Thr |
|     | 130 |     |     |     |     | 135 |     |     |     |     | 140 |     |     |     |     |
| Lys | Ala | Val | Leu | Leu | Val | Arg | Lys | Phe | Gln | Asn | Ser | Pro | Ala | Glu | Asp |
| 145 |     |     |     |     | 150 |     |     |     |     | 155 |     |     |     |     | 160 |
| Phe | Gln | Glu | Pro | Cys | Gln | Tyr | Ser | Gln | Glu | Ser | Gln | Lys | Phe | Ser | Cys |
|     |     |     |     | 165 |     |     |     |     | 170 |     |     |     |     | 175 |     |
| Gln | Leu | Ala | Val | Pro | Glu | Gly | Asp | Ser | Ser | Phe | Tyr | Ile | Val | Ser | Met |
|     |     |     | 180 |     |     |     |     | 185 |     |     |     |     | 190 |     |     |
| Cys | Val | Ala | Ser | Ser | Val | Gly | Ser | Lys | Phe | Ser | Lys | Thr | Gln | Thr | Phe |
|     |     |     | 195 |     |     |     |     | 200 |     |     |     |     | 205 |     |     |
| Gln | Gly | Cys | Gly | Ile | Leu | Gln | Pro | Asp | Pro | Pro | Ala | Asn | Ile | Thr | Val |
|     | 210 |     |     |     |     | 215 |     |     |     |     | 220 |     |     |     |     |
| Thr | Ala | Val | Ala | Arg | Asn | Pro | Arg | Trp | Leu | Ser | Val | Thr | Trp | Gln | Asp |
| 225 |     |     |     |     | 230 |     |     |     |     | 235 |     |     |     |     | 240 |
| Pro | His | Ser | Trp | Asn | Ser | Ser | Phe | Tyr | Arg | Leu | Arg | Phe | Glu | Leu | Arg |
|     |     |     |     | 245 |     |     |     |     | 250 |     |     |     |     | 255 |     |
| Tyr | Arg | Ala | Glu | Arg | Ser | Lys | Thr | Phe | Thr | Thr | Trp | Met | Val | Lys | Asp |
|     |     |     |     | 260 |     |     |     |     | 265 |     |     |     |     | 270 |     |
| Leu | Gln | His | His | Cys | Val | Ile | His | Asp | Ala | Trp | Ser | Gly | Leu | Arg | His |
|     |     | 275 |     |     |     |     | 280 |     |     |     |     | 285 |     |     |     |
| Val | Val | Gln | Leu | Arg | Ala | Gln | Glu | Glu | Phe | Gly | Gln | Gly | Glu | Trp | Ser |
|     | 290 |     |     |     |     | 295 |     |     |     |     | 300 |     |     |     |     |
| Glu | Trp | Ser | Pro | Glu | Ala | Met | Gly | Thr | Pro | Trp | Thr | Glu | Ser | Arg | Ser |
| 305 |     |     |     |     | 310 |     |     |     |     | 315 |     |     |     |     | 320 |
| Pro | Pro | Ala | Glu | Asn | Glu | Val | Ser | Thr | Pro | Met | Gln | Ala | Leu | Thr | Thr |
|     |     |     |     | 325 |     |     |     |     | 330 |     |     |     |     | 335 |     |
| Asn | Lys | Asp | Asp | Asp | Asn | Ile | Leu | Phe | Arg | Asp | Ser | Ala | Asn | Ala | Thr |
|     |     |     | 340 |     |     |     |     | 345 |     |     |     |     | 350 |     |     |
| Ser | Leu | Pro | Val | Gln | Asp | Ser | Ser | Ser | Val | Pro | Leu | Pro | Thr | Phe | Leu |
|     |     | 355 |     |     |     |     | 360 |     |     |     |     | 365 |     |     |     |
| Val | Ala | Gly | Gly | Ser | Leu | Ala | Phe | Gly | Thr | Leu | Leu | Cys | Ile | Ala | Ile |
|     | 370 |     |     |     |     | 375 |     |     |     |     | 380 |     |     |     |     |
| Val | Leu | Arg | Phe | Lys | Lys | Thr | Trp | Lys | Leu | Arg | Ala | Leu | Lys | Glu | Gly |
| 385 |     |     |     |     | 390 |     |     |     |     | 395 |     |     |     |     | 400 |

```
Lys Thr Ser Met His Pro Pro Tyr Ser Leu Gly Gln Leu Val Pro Glu
            405             410                 415
Arg Pro Arg Pro Thr Pro Val Leu Val Pro Leu Ile Ser Pro Pro Val
            420             425                 430
Ser Pro Ser Ser Leu Gly Ser Asp Asn Thr Ser Ser His Asn Arg Pro
            435             440                 445
Asp Ala Arg Asp Pro Arg Ser Pro Tyr Asp Ile Ser Asn Thr Asp Tyr
    450             455                 460
Phe Phe Pro Arg
465
```

FIG. 8B

```
Met Asn Ser Phe Ser Thr Ser Ala Phe Gly Pro Val Ala Phe Ser Leu
 1           5                    10                    15
Gly Leu Leu Leu Val Leu Pro Ala Ala Phe Pro Ala Pro Val Pro Pro
            20                   25                30
Gly Glu Asp Ser Lys Asp Val Ala Ala Pro His Arg Gln Pro Leu Thr
            35                   40              45
Ser Ser Glu Arg Ile Asp Lys Gln Ile Arg Tyr Ile Leu Asp Gly Ile
    50                   55                  60
Ser Ala Leu Arg Lys Glu Thr Cys Asn Lys Ser Asn Met Cys Glu Ser
65              70                   75                       80
Ser Lys Glu Ala Leu Ala Glu Asn Asn Leu Asn Leu Pro Lys Met Ala
                85                   90                   95
Glu Lys Asp Gly Cys Phe Gln Ser Gly Phe Asn Glu Glu Thr Cys Leu
            100                  105                 110
Val Lys Ile Ile Thr Gly Leu Leu Glu Phe Glu Val Tyr Leu Glu Tyr
        115                  120                 125
Leu Gln Asn Arg Phe Glu Ser Ser Glu Glu Gln Ala Arg Ala Val Gln
    130                  135                 140
Met Ser Thr Lys Val Leu Ile Gln Phe Leu Gln Lys Lys Ala Lys Asn
145                  150                 155                 160
Leu Asp Ala Ile Thr Thr Pro Asp Pro Thr Thr Asn Ala Ser Leu Leu
            165                  170                 175
Thr Lys Leu Gln Ala Gln Asn Gln Trp Leu Gln Asp Met Thr Thr His
            180                  185                 190
Leu Ile Leu Arg Ser Phe Lys Glu Phe Leu Gln Ser Ser Leu Arg Ala
        195                  200                 205
Leu Arg Gln Met
        210
```

FIG. 9

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 1128 base pairs
      (B) TYPE: nucleic acid
      (C) STRANDEDNESS: single
      (D) TOPOLOGY: unknown (xi) SEQUENCE DESCRIPTION: SEQ ID NO:1:

```
ATTCTGCCCT CGAGCCCACC GGGAACGAAA GAGAAGCTCT ATCTCCCCTC          50

CAGGAGCCCA GCTATGAACT CCTTCTCCAC AAGCGCCTTC GGTCCAGTTG         100

CCTTCTCCCT GGGGCTGCTC CTGGTGTTGC CTGCTGCCTT CCCTGCCCCA         150

GTACCCCCAG GAGAAGATTC CAAAGATGTA GCCGCCCCAC ACAGACAGCC         200

ACTCACCTCT TCAGAACGAA TTGACAAACA AATTCGGTAC ATCCTCGACG         250

GCATCTCAGC CCTGAGAAAG GAGACATGTA ACAAGAGTAA CATGTGTGAA         300

AGCAGCAAAG AGGCACTGGC AGAAAACAAC CTGAACCTTC CAAAGATGGC         350

TGAAAAAGAT GGATGCTTCC AATCTGGATT CAATGAGGAG ACTTGCCTGG         400

TGAAAATCAT CACTGGTCTT TTGGAGTTTG AGGTATACCT AGAGTACCTC         450

CAGAACAGAT TTGAGAGTAG TGAGGAACAA GCCAGAGCTG TCCAGATGAG         500
```

-continued

| | |
|---|---|
| TACAAAAGTC CTGATCCAGT TCCTGCAGAA AAAGGCAAAG AATCTAGATG | 550 |
| CAATAACCAC CCCTGACCCA ACCACAAATG CCAGCCTGCT GACGAAGCTG | 600 |
| CAGGCACAGA ACCAGTGGCT GCAGGACATG ACAACTCATC TCATTCTGCG | 650 |
| CAGCTTTAAG GAGTTCCTGC AGTCCAGCCT GAGGGCTCTT CGGCAAATGT | 700 |
| AGCATGGGCA CCTCAGATTG TTGTTGTTAA TGGGCATTCC TTCTTCTGGT | 750 |
| CAGAAACCTG TCCACTGGGC ACAGAACTTA TGTTGTTCTC TATGGAGAAC | 800 |
| TAAAAGTATG AGCGTTAGGA CACTATTTTA ATTATTTTA ATTTATTAAT | 850 |
| ATTTAAATAT GTGAAGCTGA GTTAATTTAT GTAAGTCATA TTTTATATTT | 900 |
| TTAAGAAGTA CCACTTGAAA CATTTTATGT ATTAGTTTTG AAATAATAAT | 950 |
| GGAAAGTGGC TATGCAGTTT GAATATCCTT TGTTTCAGAG CCAGATCATT | 1000 |
| TCTTGGAAAG TGTAGGCTTA CCTCAAATAA ATGGCTAACT TTATACATAT | 1050 |
| TTTTAAAGAA ATATTTATAT TGTATTTATA TAATGTATAA ATGGTTTTTA | 1100 |
| TACCAATAAA TGGCATTTTA AAAAATTC | 1128 |

(2) INFORMATION FOR SEQ ID NO:2:

(i) SEQUENCE CHARACTERISTICS:
        (A) LENGTH: 3319 base pairs
        (B) TYPE: nucleic acid
        (C) STRANDEDNESS: single
        (D) TOPOLOGY: unknown (xi) SEQUENCE DESCRIPTION: SEQ ID NO:2:

| | |
|---|---|
| GGCGGTCCCC TGTTCTCCCC GCTCAGGTGC GGCGCTGTGG CAGGAAGCCA | 50 |
| CCCCCTCGGT CGGCCGGTGC GCGGGGCTGT TGCGCCATCC GCTCCGGCTT | 100 |
| TCGTAACCGC ACCCTGGGAC GGCCCAGAGA CGCTCCAGCG CGAGTTCCTC | 150 |
| AAATGTTTTC CTGCGTTGCC AGGACCGTCC GCCGCTCTGA GTCATGTGCG | 200 |
| AGTGGGAAGT CGCACTGACA CTGAGCCGGG CCAGAGGGAG AGGAGCCGAG | 250 |
| CGCGGCGCGG GGCCGAGGGA CTCGCAGTGT GTGTAGAGAG CCGGGCTCCT | 300 |
| GCGGATGGGG GCTGCCCCCG GGGCCTGAGC CCGCCTGCCC GCCCACCGCC | 350 |
| CCGCCCCGCC CCTGCCACCC CTGCCGCCCG GTTCCCATTA GCCTGTCCGC | 400 |
| CTCTGCGGGA CCATGGAGTG GTAGCCGAGG AGGAAGCATG CTGGCCGTCG | 450 |
| GCTGCGCGCT GCTGGCTGCC CTGCTGGCCG CGCCGGGAGC GGCGCTGGCC | 500 |
| CCAAGGCGCT GCCCTGCGCA GGAGGTGGCA AGAGGCGTGC TGACCAGTCT | 550 |
| GCCAGGAGAC AGCGTGACTC TGACCTGCCC GGGGGTAGAG CCGGAAGACA | 600 |
| ATGCCACTGT TCACTGGGTG CTCAGGAAGC CGGCTGCAGG CTCCCACCCC | 650 |
| AGCAGATGGG CTGGCATGGG AAGGAGGCTG CTGCTGAGGT CGGTGCAGCT | 700 |
| CCACGACTCT GGAAACTATT CATGCTACCG GGCCGGCCGC CCAGCTGGGA | 750 |
| CTGTGCACTT GCTGGTGGAT GTTCCCCCCG AGGAGCCCCA GCTCTCCTGC | 800 |
| TTCCGGAAGA GCCCCCTCAG CAATGTTGTT TGTGAGTGGG GTCCTCGGAG | 850 |
| CACCCCATCC CTGACGACAA AGGCTGTGCT CTTGGTGAGG AAGTTTCAGA | 900 |
| ACAGTCCGGC CGAAGACTTC CAGGAGCCGT GCCAGTATTC CCAGGAGTCC | 950 |
| CAGAAGTTCT CCTGCCAGTT AGCAGTCCCG GAGGGAGACA GCTCTTTCTA | 1000 |
| CATAGTGTCC ATGTGCGTCG CCAGTAGTGT CGGGAGCAAG TTCAGCAAAA | 1050 |

```
CTCAAACCTT TCAGGGTTGT GGAATCTTGC AGCCTGATCC GCCTGCCAAC    1100

ATCACAGTCA CTGCCGTGGC CAGAAACCCC CGCTGGCTCA GTGTCACCTG    1150

GCAAGACCCC CACTCCTGGA ACTCATCTTT CTACAGACTA CGGTTTGAGC    1200

TCAGATATCG GGCTGAACGG TCAAAGACAT TCACAACATG GATGGTCAAG    1250

GACCTCCAGC ATCACTGTGT CATCCACGAC GCCTGGAGCG GCCTGAGGCA    1300

CGTGGTGCAG CTTCGTGCCC AGGAGGAGTT CGGGCAAGGC GAGTGGAGCG    1350

AGTGGAGCCC GGAGGCCATG GGCACGCCTT GGACAGAATC CAGGAGTCCT    1400

CCAGCTGAGA ACGAGGTGTC CACCCCCATG CAGGCACTTA CTACTAATAA    1450

AGACGATGAT AATATTCTCT TCAGAGATTC TGCAAATGCG ACAAGCCTCC    1500

CAGTGCAAGA TTCTTCTTCA GTACCACTGC CCACATTCCT GGTTGCTGGA    1550

GGGAGCCTGG CCTTCGGAAC GCTCCTCTGC ATTGCCATTG TTCTGAGGTT    1600

CAAGAAGACG TGGAAGCTGC GGGCTCTGAA GGAAGGCAAG ACAAGCATGC    1650

ATCCGCCGTA CTCTTTGGGG CAGCTGGTCC CGGAGAGGCC TCGACCCACC    1700

CCAGTGCTTG TTCCTCTCAT CTCCCCACCG GTGTCCCCCA GCAGCCTGGG    1750

GTCTGACAAT ACCTCGAGCC ACAACCGACC AGATGCCAGG GACCCACGGA    1800

GCCCTTATGA CATCAGCAAT ACAGACTACT TCTTCCCCAG ATAGCTGGCT    1850

GGGTGGCACC AGCAGCCTGG ACCCTGTGGA TGACAAAACA CAAACGGGCT    1900

CAGCAAAAGA TGCTTCTCAC TGCCATGCCA GCTTATCTCA GGGGTGTGCG    1950

GCCTTTGGCT TCACGAAGA GCCTTGCGGA AGGTTCTACG CCAGGGGAAA    2000

ATCAGCCTGC TCCAGCTGTT CAGCTGGTTG AGGTTTCAAA CCTCCCTTTC    2050

CAAATGCCCA GCTTAAAGGG GTTAGAGTGA ACTTGGGCCA CTGTGAAGAG    2100

AACCATATCA AGACTCTTTG GACACTCACA CGGACACTCA AAAGCTGGGC    2150

AGGTTGGTGG GGGCCTCGGT GTGGAGAAGC GGCTGGCAGC CCACCCCTCA    2200

ACACCTCTGC ACAAGCTGCA CCCTCAGGCA GGTGGGATGG ATTTCCAGCC    2250

AAAGCCTCCT CCAGCCGCCA TGCTCCTGGC CCACTGCATC GTTTCATCTT    2300

CCAACTCAAA CTCTTAAAAC CCAAGTGCCC TTAGCAAATT CTGTTTTTCT    2350

AGGCCTGGGG ACGGCTTTTA CTTAAACGCC AAGGCCTGGG GGAAGAAGCT    2400

CTCTCCTCCC TTTCTTCCCT ACAGTTCAAA AACAGCTGAG GGTGAGTGGG    2450

TGAATAATAC AGTATGTCAG GGCCTGGTCG TTTTCAACAG AATTATAATT    2500

AGTTCCTCAT TAGCAGTTTT GCCTAAATGT GAATGATGAT CCTAGGCATT    2550

TGCTGAATAC AGAGGCAACT GCATTGGCTT TGGGTTGCAG GACCTCAGGT    2600

GAGAAGCAGA GGAAGGAGAG GAGAGGGGCA CAGGGTCTCT ACCATCCCCT    2650

GTAGAGTGGG AGCTGAGTGG GGGATCACAG CCTCTGAAAA CCAATGTTCT    2700

CTCTTCTCCA CCTCCCACAA AGGAGAGCTA GCAGCAGGGA GGGCTTCTGC    2750

CATTTCTGAG ATCAAAACGG TTTTACTGCA GCTTTGTTTG TTGTCAGCTG    2800

AACCTGGGTA ACTAGGGAAG ATAATATTAA GGAAGACAAT GTGAAAAGAA    2850

AAATGAGCCT GGCAAGAATG CGTTTAAACT TGGTTTTTAA AAAACTGCTG    2900

ACTGTTTTCT CTTGAGAGGG TGGAATATCC AATATTCGCT GTGTCAGCAT    2950

AGAAGTAACT TACTTAGGTG TGGGGGAAGC ACCATAACTT TGTTTAGCCC    3000

AAAACCAAGT CAAGTGAAAA AGGAGGAAGA GAAAAAATAT TTTCCTGCCA    3050
```

| | |
|---|---:|
| GGCATGGAGG CCCACGCACT TCGGGAGGTC GAGGCAGGAG GATCACTTGA | 3100 |
| GTCCAGAAGT TTGAGATCAG CCTGGGCAAT GTGATAAAAC CCCATCTCTA | 3150 |
| CAAAAAGCAT AAAAATTAGC CAAGTGTGGT AGAGTGTGCC TGAAGTCCCA | 3200 |
| GATACTTGGG GGGCTGAGGT GGGAGGATCT CTTGAGCCTG GGAGGTCAAG | 3250 |
| GCTGCAGTGA GCCGAGATTG CACCACTGCA CTCCAGCCTG GGGTGACAGA | 3300 |
| GCAAGTGAGA CCCTGTCTC | 3319 |

(2) INFORMATION FOR SEQ ID NO:3:

(i) SEQUENCE CHARACTERISTICS:
        (A) LENGTH: 1486 base pairs
        (B) TYPE: nucleic acid
        (C) STRANDEDNESS: single
        (D) TOPOLOGY: unknown (xi) SEQUENCE DESCRIPTION: SEQ ID NO:3:

| | |
|---|---:|
| ATTAGCCTGT CCGCCTCTGC GGGACCATGG AGTGGTAGCC GAGGAGGAAG | 50 |
| CATGCTGGCC GTCGGCTGCG CGCTGCTGGC TGCCCTGCTG GCCGCGCCGG | 100 |
| GAGCGGCGCT GGCCCCAAGG CGCTGCCCTG CGCAGGAGGT GGCGAGAGGC | 150 |
| GTGCTGACCA GTCTGCCAGG AGACAGCGTG ACTCTGACCT GCCCGGGGGT | 200 |
| AGAGCCGGAA GACAATGCCA CTGTTCACTG GGTGCTCAGG AAGCCGGCTG | 250 |
| CAGGCTCCCA CCCCAGCAGA TGGGCTGGCA TGGGAAGGAG GCTGCTGCTG | 300 |
| AGGTCGGTGC AGCTCCACGA CTCTGGAAAC TATTCATGCT ACCGGGCCGG | 350 |
| CCGCCCAGCT GGGACTGTGC ACTTGCTGGT GGATGTTCCC CCCGAGGAGC | 400 |
| CCCAGCTCTC CTGCTTCCGG AAGAGCCCCC TCAGCAATGT TGTTTGTGAG | 450 |
| TGGGGTCCTC GGAGCACCCC ATCCCTGACG ACAAAGGCTG TGCTCTTGGT | 500 |
| GAGGAAGTTT CAGAACAGTC CGGCCGAAGA CTTCCAGGAG CCGTGCCAGT | 550 |
| ATTCCCAGGA GTCCCAGAAG TTCTCCTGCC AGTTAGCAGT CCCGGAGGGA | 600 |
| GACAGCTCTT TCTACATAGT GTCCATGTGC GTCGCCAGTA GTGTCGGGAG | 650 |
| CAAGTTCAGC AAAACTCAAA CCTTTCAGGG TTGTGGAATC TTGCAGCCTG | 700 |
| ATCCGCCTGC CAACATCACA GTCACTGCCG TGGCCAGAAA CCCCCGCTGG | 750 |
| CTCAGTGTCA CCTGGCAAGA CCCCCACTCC TGGAACTCAT CTTTCTACAG | 800 |
| ACTACGGTTT GAGCTCAGAT ATCGGGCTGA ACGGTCAAAG ACATTCACAA | 850 |
| CATGGATGGT CAAGGACCTC CAGCATCACT GTGTCATCCA CGACGCCTGG | 900 |
| AGCGGCCTGA GGCACGTGGT GCAGCTTCGT GCCCAGGAGG AGTTCGGGCA | 950 |
| AGGCGAGTGG AGCGAGTGGA GCCCGGAGGC CATGGGCACG CCTTGGACAG | 1000 |
| AATCCAGGAG TCCTCCAGCT GAGAACGAGG TGTCCACCCC CATGCAGGCA | 1050 |
| CTTACTACTA ATAAAGACGA TGATAATATT CTCTTCAGAG ATTCTGCAAA | 1100 |
| TGCGACAAGC CTCCCAGTGC AAGATTCTTC TTCAGTACCA CTGCCCACAT | 1150 |
| TCCTGGTTGC TGGAGGGAGC CTGGCCTTCG GAACGCTCCT CTGCATTGCC | 1200 |
| ATTGTTCTGA GGTTCAAGAA GACGTGGAAG CTGCGGGCTC TGAAGGAAGG | 1250 |
| CAAGACAAGC ATGCATCCGC CGTACTCTTT GGGGCAGCTG GTCCCGGAGA | 1300 |
| GGCCTCGACC CACCCCAGTG CTTGTTCCTC TCATCTCCCC ACCGGTGTCC | 1350 |
| CCCAGCAGCC TGGGGTCTGA CAATACCTCG AGCCACAACC GACCAGATGC | 1400 |

| | |
|---|---|
| CAGGGACCCA CGGAGCCCTT ATGACATCAG CAATACAGAC TACTTCTTCC | 1450 |
| CCAGATAGCT GGCTGGGTGG CACCAGCAGC CTGGAC | 1486 |

(2) INFORMATION FOR SEQ ID NO:4:

(i) SEQUENCE CHARACTERISTICS:
        (A) LENGTH: 3085 base pairs
        (B) TYPE: nucleic acid
        (C) STRANDEDNESS: single
        (D) TOPOLOGY: unknown (xi) SEQUENCE DESCRIPTION: SEQ ID NO: 4:

| | |
|---|---|
| GAGCAGCCAA AAGGCCCGCG GAGTCGCGCT GGGCCGCCCC GGCGCAGCTG | 50 |
| AACCGGGGGC CGCGCCTGCC AGGCCGACGG GTCTGGCCCA GCCTGGCGCC | 100 |
| AAGGGGTTCG TGCGCTGTGG AGACGCGGAG GGTCGAGGCG GCGCGGCCTG | 150 |
| AGTGAAACCC AATGGAAAAA GCATGACATT TAGAAGTAGA AGACTTAGCT | 200 |
| TCAAATCCCT ACTCCTTCAC TTACTAATTT TGTGATTTGG AAATATCCGC | 250 |
| GCAAGATGTT GACGTTGCAG ACTTGGGTAG TGCAAGCCTT GTTTATTTTC | 300 |
| CTCACCACTG AATCTACAGG TGAACTTCTA GATCCATGTG GTTATATCAG | 350 |
| TCCTGAATCT CCAGTTGTAC AACTTCATTC TAATTTCACT GCAGTTTGTG | 400 |
| TGCTAAAGGA AAAATGTATG GATTATTTTC ATGTAAATGC TAATTACATT | 450 |
| GTCTGGAAAA CAAACCATTT TACTATTCCT AAGGAGCAAT ATACTATCAT | 500 |
| AAACAGAACA GCATCCAGTG TCACCTTTAC AGATATAGCT TCATTAAATA | 550 |
| TTCAGCTCAC TTGCAACATT CTTACATTCG GACAGCTTGA ACAGAATGTT | 600 |
| TATGGAATCA CAATAATTTC AGGCTTGCCT CCAGAAAAAC CTAAAAATTT | 650 |
| GAGTTGCATT GTGAACGAGG GGAAGAAAAT GAGGTGTGAG TGGGATGGTG | 700 |
| GAAGGGAAAC ACACTTGGAG ACAAACTTCA CTTTAAAATC TGAATGGGCA | 750 |
| ACACACAAGT TTGCTGATTG CAAAGCAAAA CGTGACACCC CCACCTCATG | 800 |
| CACTGTTGAT TATTCTACTG TGTATTTTGT CAACATTGAA GTCTGGGTAG | 850 |
| AAGCAGAGAA TGCCCTTGGG AAGGTTACAT CAGATCATAT CAATTTTGAT | 900 |
| CCTGTATATA AAGTGAAGCC CAATCCGCCA CATAATTTAT CAGTGATCAA | 950 |
| CTCAGAGGAA CTGTCTAGTA TCTTAAAATT GACATGGACC AACCCAAGTA | 1000 |
| TTAAGAGTGT TATAATACTA AAATATAACA TTCAATATAG GACCAAAGAT | 1050 |
| GCCTCAACTT GGAGCCAGAT TCCTCCTGAA GACACAGCAT CCACCCGATC | 1100 |
| TTCATTCACT GTCCAAGACC TTAAACCTTT TACAGAATAT GTGTTTAGGA | 1150 |
| TTCGCTGTAT GAAGGAAGAT GGTAAGGGAT ACTGGAGTGA CTGGAGTGAA | 1200 |
| GAAGCAAGTG GGATCACCTA TGAAGATAGA CCATCTAAAG CACCAAGTTT | 1250 |
| CTGGTATAAA ATAGATCCAT CCCATACTCA AGGCTACAGA ACTGTACAAC | 1300 |
| TCGTGTGGAA GACATTGCCT CCTTTTGAAG CCAATGGAAA AATCTTGGAT | 1350 |
| TATGAAGTGA CTCTCACAAG ATGGAAATCA CATTTACAAA ATTACACAGT | 1400 |
| TAATGCCACA AAACTGACAG TAAATCTCAC AAATGATCGC TATCTAGCAA | 1450 |
| CCCTAACAGT AAGAAATCTT GTTGGCAAAT CAGATGCAGC TGTTTTAACT | 1500 |
| ATCCCTGCCT GTGACTTTCA AGCTACTCAC CCTGTAATGG ATCTTAAAGC | 1550 |
| ATTCCCCAAA GATAACATGC TTTGGGTGGA ATGGACTACT CCAAGGGAAT | 1600 |

```
CTGTAAAGAA ATATATACTT GAGTGGTGTG TGTTATCAGA TAAAGCACCC        1650

TGTATCACAG ACTGGCAACA AGAAGATGGT ACCGTGCATC GCACCTATTT        1700

AAGAGGGAAC TTAGCAGAGA GCAAATGCTA TTTGATAACA GTTACTCCAG        1750

TATATGCTGA TGGACCAGGA AGCCCTGAAT CCATAAAGGC ATACCTTAAA        1800

CAAGCTCCAC CTTCCAAAGG ACCTACTGTT CGGACAAAAA AGTAGGGAA         1850

AAACGAAGCT GTCTTAGAGT GGGACCAACT TCCTGTTGAT GTTCAGAATG        1900

GATTTATCAG AAATTATACT ATATTTTATA GAACCATCAT TGGAAATGAA        1950

ACTGCTGTGA ATGTGGATTC TTCCCACACA GAATATACAT TGTCCTCTTT        2000

GACTAGTGAC ACATTGTACA TGGTACGAAT GGCAGCATAC ACAGATGAAG        2050

GTGGGAAGGA TGGTCCAGAA TTCACTTTTA CTACCCCAAA GTTTGCTCAA        2100

GGAGAAATTG AAGCCATAGT CGTGCCTGTT TGCTTAGCAT TCCTATTGAC        2150

AACTCTTCTG GGAGTGCTGT TCTGCTTTAA TAAGCGAGAC CTAATTAAAA        2200

AACACATCTG GCCTAATGTT CCAGATCCTT CAAAGAGTCA TATTGCCCAG        2250

TGGTCACCTC ACACTCCTCC AAGGCACAAT TTTAATTCAA AAGATCAAAT        2300

GTATCCAGAT GGCAATTTCA CTGATGTAAG TGTTGTGGAA ATAGAAGCAA        2350

ATGACAAAAA GCCTTTTCCA GAAGATCTGA AATCATTGGA CCTGTTCAAA        2400

AAGGAAAAAA TTAATACTGA AGGACACAGC AGTGGTATTG GGGGGTCTTC        2450

ATGCATGTCA TCTTCTAGGC CAAGCATTTC TAGCAGTGAT GAAAATGAAT        2500

CTTCACAAAA CACTTCGAGC ACTGTCCAGT ATTCTACCGT GGTACACAGT        2550

GGCTACAGAC ACCAAGTTCC GTCAGTCCAA GTCTTCTCAA GATCCGAGTC        2600

TACCCAGCCC TTGTTAGATT CAGAGGAGCG GCCAGAAGAT CTACAATTAG        2650

TAGATCATGT AGATGGCGGT GATGGTATTT TGCCCAGGCA ACAGTACTTC        2700

AAACAGAACT GCAGTCAGCA TGAATCCAGT CCAGATATTT CACATTTGA         2750

AAGGTCAAAG CAAGTTTCAT CAGTCAATGA GGAAGATTTT GTTAGACTTA        2800

AACAGCAGAT TTCAGATCAT ATTTCACAAT CCTGTGGATC TGGGCAAATG        2850

AAAATGTTTC AGGAAGTTTC TGCAGCAGAT GCTTTTGGTC CAGGTACTGA        2900

GGACAAGTA GAAAGATTTG AAACAGTTGG CATGGAGGCT GCGACTGATG         2950

AAGGCATGCC TAAAAGTTAC TTACCACAGA CTGTACGGCA AGGCGGCTAC        3000

ATGCCTCAGT GAAGGACTAG TAGTTCCTGC TACAACTTCA GCAGTACCTA        3050

TAAAGTAAAG CTAAAATGAT TTTATCTGTG AATTC                        3085
```

(2) INFORMATION FOR SEQ ID NO:5:

(i) SEQUENCE CHARACTERISTICS:
        (A) LENGTH: 468 amino acids
        (B) TYPE: amino acid
        (D) TOPOLOGY: unknown (xi) SEQUENCE DESCRIPTION: SEQ ID NO: 5:

```
Met Leu Ala Val Gly Cys Ala Leu Leu Ala Ala Leu Leu Ala Ala Pro
                 5                  10                  15

Gly Ala Ala Leu Ala Pro Arg Arg Cys Pro Ala Gln Glu Val Ala Arg
             20                  25                  30

Gly Val Leu Thr Ser Leu Pro Gly Asp Ser Val Thr Leu Thr Cys Pro
         35                  40                  45
```

```
Gly Val Glu Pro Glu Asp Asn Ala Thr Val His Trp Val Leu Arg Lys
    50                  55                  60

Pro Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
                100                 105                 110

Pro Pro Glu Glu Pro Gln Leu Ser Cys Phe Arg Lys Ser Pro Leu Ser
            115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
                180                 185                 190

Cys Val Ala Ser Ser Val Gly Ser Lys Phe Ser Lys Thr Gln Thr Phe
    195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
                260                 265                 270

Leu Gln His His Cys Val Ile His Asp Ala Trp Ser Gly Leu Arg His
                275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
                340                 345                 350

Ser Leu Pro Val Gln Asp Ser Ser Val Pro Leu Pro Thr Phe Leu
                355                 360                 365

Val Ala Gly Gly Ser Leu Ala Phe Gly Thr Leu Leu Cys Ile Ala Ile
    370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
                420                 425                 430

Ser Pro Ser Ser Leu Gly Ser Asp Asn Thr Ser Ser His Asn Arg Pro
            435                 440                 445

Asp Ala Arg Asp Pro Arg Ser Pro Tyr Asp Ile Ser Asn Thr Asp Tyr
            450                 455                 460
```

```
Phe Phe Pro Arg
465

(2) INFORMATION FOR SEQ ID NO:6:

(i) SEQUENCE CHARACTERISTICS:
        (A) LENGTH: 212 amino acids
        (B) TYPE: amino acid
        (D) TOPOLOGY: unknown (xi) SEQUENCE DESCRIPTION: SEQ ID NO: 6:

Met Asn Ser Phe Ser Thr Ser Ala Phe Gly Pro Val Ala Phe Ser Leu
 1               5                  10                  15

Gly Leu Leu Leu Val Leu Pro Ala Ala Phe Pro Ala Pro Val Pro Pro
                20                  25                  30

Gly Glu Asp Ser Lys Asp Val Ala Ala Pro His Arg Gln Pro Leu Thr
            35                  40                  45

Ser Ser Glu Arg Ile Asp Lys Gln Ile Arg Tyr Ile Leu Asp Gly Ile
50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
            115                 120                 125

Leu Gln Asn Arg Phe Glu Ser Ser Glu Glu Gln Ala Arg Ala Val Gln
130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
            195                 200                 205

Leu Arg Gln Met
            210

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: unknown (xi) SEQUENCE DESCRIPTION: SEQ ID NO:7:

GGAGGCTGTA GGCATAAATT GGTCTGCGC                                              29

(2) INFORMATION FOR SEQ ID NO:8:

(i) SEQUENCE CHARACTERISTICS:
        (A) LENGTH: 39 base pairs
        (B) TYPE: nucleic acid
        (C) STRANDEDNESS: single
        (D) TOPOLOGY: unknown (xi) SEQUENCE DESCRIPTION: SEQ ID NO:8:
```

```
CCCGAGATTG AGATCTTCTG CGACGCGGCG ATTGAGACC                        39

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: unknown (ii) SEQUENCE DESCRIPTION: SEQ ID NO:9:

CGGGATCCAT GGGAGGTTGG TCATC                                      25

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: unknown (xi) SEQUENCE DESCRIPTION: SEQ ID NO:10:

GGAATTCCAC TGCATGGC                                              18
```

PHARMACEUTICAL COMPOSITION FOR TREATING HEPATITIS B VIRUS (HBV) INFECTION

BACKGROUND AND SUMMARY OF THE INVENTION

The present invention relates to pharmaceutical compositions for the treatment of hepatitis B virus (HBV) infection.

HBV infection in humans can cause chronic liver disease which will, in some cases, proceed to hepatocellular carcinoma. The initial steps of HBV attachment to cells and the targeting of the viral genome to the host cell nucleus have yet to be deciphered. The specific receptor for HBV has not so far been identified, even though various serum proteins and cellular membrane glycoproteins have been suggested as mediators of cell penetration or viral receptors. HBV envelope proteins were reported to contain residues which interact with polymerized albumin [P. Pontisso, et al., *Journal of Virology*, Vol. 63, No. 1981-1, p. 988 (1981)] or with soluble transferrin [M. Gagliardi, et al., *Eur. J. Immunol.*, Vol. 24, pp. 1372–1376 (1994)], enabling viral penetration of cells via their respective receptors, probably in a nonspecific manner.

In a study reported by Neurath, et al. [A. Neurath, et al., *J. Exp. Med.*, Vol. 175, pp. 461–469 (1992)] hIL-6 was shown to bind the pS1 (aa 21–47) segment of the HBV envelope. Putative candidates for the HBV receptor were recently reported, including Annexin V (endohexin II) [K. Hertogs, et al., *Virology*, Vol. 197, pp. 549–557 (1993)]; apolipoprotein H [H. Mehdi, et al., *Journal of Virology*, Vol. 68, pp. 2415–2424 (1994)]; and asialoglycoprotein receptor [U. Treichel, et al., *Journal of General Virology*, Vol. 75, pp. 3021–3029 (1994)].

Binding experiments have demonstrated that the pre-S1 (pS1) region of the viral envelope protein contains a recognition site for the host cell [A. R. Neurath, et al., *Cell*, Vol. 46, pp. 429–436 (1986); M. Petit, et al., *Virology*, Vol. 180, pp. 483–491 (1990); M. Petit, et al., *Virology*, Vol. 197, pp. 211–222 (1992)]. Although previous studies had suggested that HepG2 cells [R. Bchini, et al., *Journal of Virology*, Vol. 64, pp. 3025–3032 (1991)] and human hepatocytes [P. Gripon, et al., *Journal of Virology*, Vol. 62, pp. 4136–4143 (1988); T. Ochiya, et al., *Proc. Natl. Acad. Sci. U.S.A.*, Vol. 86, pp. 1875–1879 (1989); P. Gripon, et al., *Virology*, Vol. 192, pp. 534–540 (1993); P. Galle, et al., *Gastroenterology*, Vol. 106, pp. 664–673 (1994)] could support HBV infection in vitro, no cellular receptor has as yet been defined in either system, and these models were of low experimental reproducibility.

In current reports, it has been shown that a chimeric mouse, generated by using Beige/Nude/X linked immunodeficient (BNX) mice, preconditioned by total body irradiation (12Gy) and reconstituted with severe combined immunodeficient (SCID) mice bone marrow (BM) cells, is permissive for normal human T and B cells [I. Lubin, et al., *Science*, Vol. 252, pp. 427–431 (1991)], as well as for normal human liver tissue [E. Galun, et al., *Journal of Infectious Diseases*, Vol. 175, pp. 25–30 (1995)]. Hepatitis C virus (HCV) viremia was detectable for up to two months, after implantation under the kidney capsule of the BNX>SCID chimeric animals of either a human liver fragment with preexisting HCV infection, or normal human liver tissue following incubation ex-vivo of the transplanted liver fragment with HCV-positive sera [E. Galun, et al., ibid.]. Heretofore, one of the major obstacles in elucidating the initial steps of HBV infection and the assessment of antiviral agents, has been the lack of a small animal model. Using the techniques referred to above, it was possible to develop SCID>BNX animals which sustain HBV viremia following the implantation of an ex-vivo HBV DNA-positive sera incubation with liver tissue. The method in which the animals were prepared for the experiments described herein, and the surgical technique for transplantation, are similar to those previously reported [E. Galun, et al., ibid.].

As will be described below, it has now been found, using a chimeric animal model, that human interleukin 6 (hIL6) is essential for HBV infection. Having identified that hIL6 serves as an essential bridge for HBV infection, the invention now provides a pharmaceutical composition for the treatment of hepatitis B virus infection, comprising an amount of a soluble active agent which interacts with at least one of the binding sites between hIL6 and pS1 and between hIL6 and hepatocytes and other HBV-permissive cells, said active agent being present in sufficient amount to competitively bind to at least one of said sites and thereby to prevent hIL6-mediated HBV infection of hepatocytes and other HBV-permissive cells.

In a first preferred embodiment of the present invention, there is provided a pharmaceutical composition for the treatment of hepatitis B virus (HBV) infection, comprising an amount of soluble gp80 and/or gp130 receptor sites sufficient to inhibit the binding of hIL6 to hepatocytes and other HBV-permissive cells.

In a second preferred embodiment of the present invention, there is provided a pharmaceutical composition for the treatment of HBV infection, comprising an amount of soluble amino acid sequences corresponding to amino acids 21 to 46 of pS1 to block the interaction of HBV with hIL6.

In a third preferred embodiment of the present invention, there is provided a pharmaceutical composition for the treatment of HBV infection, comprising an amount of a soluble ligand selected from the group consisting of peptides LYS41-ALA56, GLY77-GLU95 and GLN153-HIS165 to block the interaction of hIL6 with hepatocytes and other HBV-permissive cells.

In a fourth preferred embodiment of the present invention, there is provided a pharmaceutical composition for the treatment of HBV infection, comprising hIL6 conjugated with an anti-viral agent.

With specific reference now to the examples and figures in detail, it is stressed that the particulars described and shown are by way of example and for purposes of illustrative discussion of the preferred embodiments of the present invention only, and are presented in the cause of providing what is believed to be the most useful and readily understood description of the principles and conceptual aspects of the invention. In this context, it is to be noted that only subject matter embraced in the scope of the claims appended hereto, whether in the manner defined in the claims or in a manner similar thereto and involving the main features, as defined in the claims, is intended to be included in the scope of the present invention.

In the drawings:

The file of this patent contains at least one drawing executed in color. Copies of this patent with color drawings are provided to the Patent and Trademark Office with payment of the necessary fee.

Figure 2D:
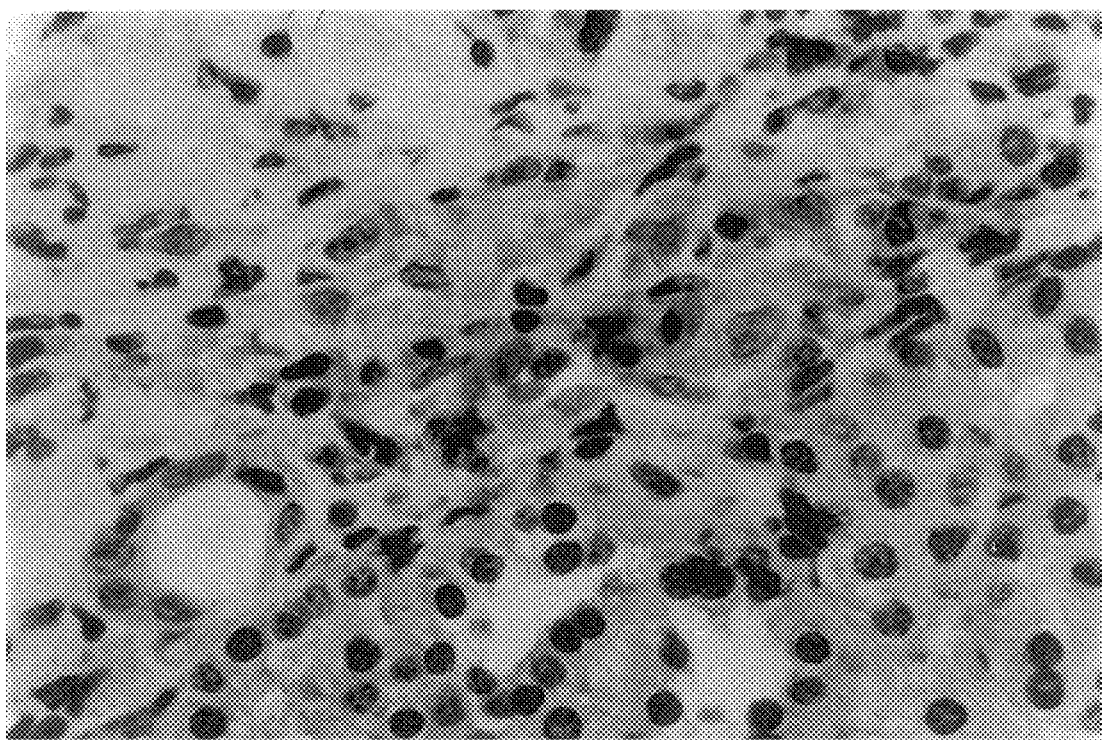
Figure 3:
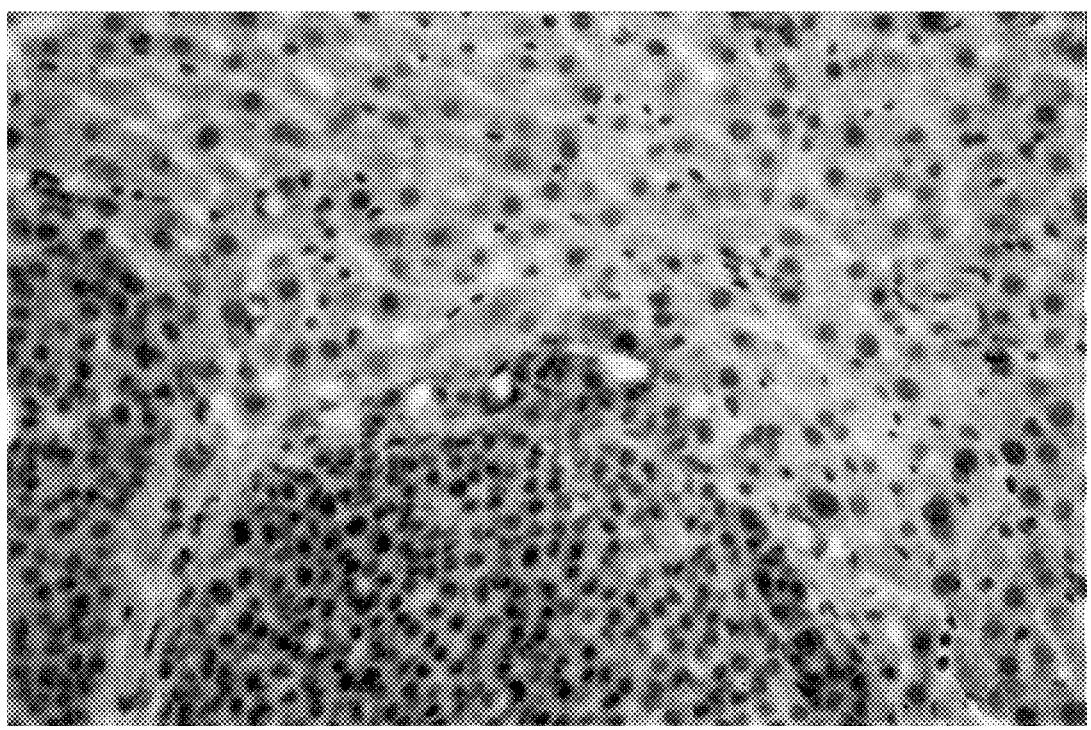

FIG. 1 illustrates a pre-infected liver fragment from a HBV DNA-positive patient, one month after sub-capsular implantation in a SCID>BNX chimeric mouse, stained for HBsAg;

FIGS. 2A–D shows that hIL6 mediates HBV viremia in SCID>BNX chimeric mice transplanted with human tissue; and FIG. 3 illustrates the liver histology of a HepG2-hIL-6R tumor, which developed one month following intrasplenic injection into a SCID>BNX chimeric mouse (H and E staining);

FIG. 4 provides the nucleotide sequence for hIL-6 mRNA;

FIGS. 5a and 5b provide the nucleotide sequence for hIL-6 receptor mRNA;

FIG. 6 provides the nucleotide sequence for the IL-6 receptor;

FIGS. 7a and 7b provide the nucleotide sequence for gp130;

FIG. 8 provides the amino acid sequence for hIL-6 receptor alpha; and

FIG. 9 provides the amino acid sequence for IL-6.

DETAILED DESCRIPTION OF THE INVENTION

EXAMPLES

Human liver tissue was taken from patients undergoing liver surgery for liver diseases, who had HBV viremia of $10^7$–$10^9$ parciles/ml with positive HBV DNA in the liver tissue. The liver tissue was implanted under the kidney capsule of the chimeric animals. Although HBsAg was easily detected in pre-infected HBV DNA positive/HBeAg positive transplanted tissue (FIG. 1), 1–3 months after liver fragment implantation HBV sequences were undetectable by PCR (applyin primers spanning the viral core gene as well as the envelope region, at the a determinant of the HBsAg) in any of these experiments. Furthermore, intravenous or intraperitoneal (i.p.) injection of 200 μl of high-titer HBV particles ($>10^8$/ml) following the transplantation of a normal human liver fragment, failed to generate HBV DNA sequences during the next 30 days (data not shown).

Lymphocytes, positive for HBV DNA by dot blot hybridization, were separated by lymphopheresis (Baxter Fenwell CS-3000 Pulse Blood Cell Separators, Deerfield, Ill., U.S.A.) from a patient with HBV-related chronic liver disease whose sera were positive for HBV DNA and HBeAg. Forty million HBV DNA-positive lymphocytes were injected i.p. to each mouse, subsequent to transplantation of normal human liver at the subcapsular site of the kidney. HBV sequences were not detected in the sera of these animals during the following 21 days.

Although the primary infection site for HBV is hepatocytes, lymphocytes and endothelial cells have both been shown to harbor HBV transcripts and viral-related proteins [J. Romet-Lemonne, et al., Science, Vol. 221, pp. 667–669 (1983); H. Blum, et al., Proc. Natl. Acad. Sci. U.S.A., Vol. 80, pp. 6685–6688 (1983); E. Galun, et al., American Journal of Pathology, Vol. 145, pp. 1001–1007 (1994)], suggesting a common specific cell membrane receptor mechanism supporting viral penetration. This mechanism would prevent infection of receptor negative cells, despite their being permissive for HBV replication by transfection [E. Galun, et al., Journal of General Virology, Vol. 73, pp. 173–178 (1992)]. All three primary cell types hosting HBV naturally, i.e., hepatocytes, lymphocytes and endothelial cells, respond to hIL6 through the human IL6 receptor (hIL6R) which is expressed on their cell membranes [A. Mackiewicz, et al., The Journal of Immunology, Vol. 149, pp. 2021–2027 (1992); J. Bauer, et al., FEBS Letter, Vol. 249, pp. 27–30 (1989); T. Kishimoto, et al., Science, Vol. 258, p. 593 (1992)]. Furthermore, as previously shown, hIL6 binds to HBV through pS1.

A fragment of normal human liver from a patient with no indication of any HBV-related markers or disease, was incubated ex-vivo with a high titer HBV DNA-positive serum prior to transplantation under the kidney capsule of the chimeric animals. HBV DNA sequences were undetectable by PCR from two different genomic regions in any of these animals during the month following transplantation. Results are shown in FIG. 2A. These results were reproduced in additional experiments in over 50 mice, using four different HBV DNA-positive sera.

However, when liver tissue originating from the same patients was incubated ex-vivo with the above-mentioned HBV DNA-positive sera together with hIL6, HBV DNA sequences were detected from day 16 to day 31, in sera of about 50% of the transplanted animals. These results are shown in FIG. 2B.

Similar results were obtained in experiments conducted under the above-stated conditions, using additional HBV DNA sera and liver tissue from different sources. In these experiments, HBV DNA sequences could be detected up to day 60 following transplantation (results not shown).

Pre-exposure of liver tissue to hIL6 prior to incubation with HBV ex-vivo, increased infection to about 90% of the animals. Animals positive for HBV sequences in serum at day 31 were also positive for HBsAg in the implanted hepatocytes, as shown in FIG. 2D. Liver fragments incubated ex-vivo with HBV under the above conditions and fixed for immunohistochemical analysis prior to transplantation were negative for HBsAg (results not shown).

To further assess the role of hIL6 in supporting HBV infection, a human hepatoblastoma cell line HepG2 (ATCC HB 8065), an HepG2-derived, stably transfected hIL6R cell line, a null hIL6R (a cell line which does not express hIL6R) named HepG2-PDI and an hIL6 producing line named HepG2-hIL6 [S. Rose-John, et al., The Journal of Biological Chemistry, Vol. 268, pp. 22084–22091 (1993)] were incubated with HBV DNA-positive sera, with or without hIL6. Following incubation, the various mixtures were injected intrasplenically to the chimeric mice to generate HCC foci in the liver, as shown in FIG. 3. The results of these experiments are summarized below in Table 1.

TABLE 1

HBV-DNA as detected by PCR in sera of chimeric mice following intrasplenic injection of HBV, with or without hIL6, after incubation with HepG2-derived cell lines

| Cell Line | HepG$_2$ hIL6R | HepG$_2$ PDI | HepG$_2$ | HepG$_2$ hIL6 |
|---|---|---|---|---|
| hIL6 | + − | + − | + − | + − |
| HBV-DNA PCR product | + − | + − | + +/− | + + |

Method:

All cell lines grew in T25 flasks supplemented with DMEM medium, enriched with 10% fetal bovine serum. For infection experiments, cells were trypsinized and washed twice with PBS, followed by incubation with HBV-positive human sera ($10^8$ virions/ml) in the presence or absence of hIL6 (500 ng/ml) in 1–2 ml of DMEM. After 2–4 h incubation at 37° C., $4\times10^6$ cells/ml, 0.5 ml/mouse were injected intrasplenically to 8–10 SCID>BNX mice in each group. Animals were splenectomized following the injection.

Mice were bled at two weekly intervals for 3 months, and DNA was extracted from 100 µl sera. The DNA was subjected to PCR amplification. The DNA extraction and the PCR method applied are described in the legend of FIG. 2. Table 1 summarizes three experiments.

In mice implanted with HepG2-hIL6R cells (which have about one log higher expression of the receptor than HepG2 cells) subsequent to incubation with HBV in the presence of hIL6, HBV-DNA sequences could be detected in serum 13 days after transplantation, whereas HBV sequences were not detected in the sera of mice who underwent the same procedure without the presence of hIL6. Similar results were obtained in experiments using HepG2-PDI cells. These cells do not express the gp 80 binding protein subunit of the hIL6R on the cell membrane [S. Rose-John, et al., ibid.; M. Ehlers, et al., *The Journal of Immunology*, Vol. 153, p. 1744 (1994)], however, they do express the signal transduction gp 130 subunit of the receptor, which is essential for efficient internaliztion of hIL6 [E. Dittrich, et al., *The Journal of Biological Chemistry*, Vol. 269, pp. 10914–19020 (1994)].

In experiments of the same design, using HepG2 cells in the presence and also in the absence of hIL6, HBV sequences could be detected in a number of murine sera. These results are similar to those previously reported by Petit, et al. [R. Bchini, et al., ibid.], showing a low reproducibility in which only three sera supported HBV infection of HepG2 cells in-vitro, out of a total of 55 different serum samples taken from HBV DNA-positive patients. The HepG2-hIL6 cell line, which produces hIL6, generated HBV sequences in mice sera following incubation with the virus, with or without external supplementation of hIL6.

When the liver fragment was incubated ex-vivo with HBV-DNA positive sera in the presence of commercially available human polyclonal anti-HBs viral neutralizing antibodies (HBIG, Hepatect®, Biotest Pharma GmbH, Dreicich. Germany), HBV-DNA was observed at day 11 following transplantation only in 48% (10/21) of mice, as compared to 78% (14/18) of the untreated mice group (Table 2).

TABLE 2

Inhibition of infection - effect of anti-HBs antibodies effect on HBV-DNA levels in sera of chimeric mice transplanted with human liver fragments infected ex vivo with HBV

| Treatment Group | Mice Positive for HBV-DNA (%) |
|---|---|
| Untreated | 14/18 (78) |
| HBIG Treatment | 10/21 (48) |

Method:

For antibody treatment, HBV-DNA positive serum (0.5 ml) was incubated with 100 IU of HBIG for 2 hours at 25° C. Human liver fragments were then added to the untreated or HBIG treated HBV-DNA positive serum according to the same protocol as described above, followed by implantation under the kidney capsule of the chimeric animal. Mice sera were analyzed for the presence of HBV-DNA sequences 11 days after transplantation.

Referring again to the figures, FIG. 1 shows pre-infected liver fragment from a HBV DNA-positive patient, one month after sub-capsular implantation in a SCID>BNX chimeric mouse, stained for HBsAg.

From FIG. 2 it can be seen that hIL6 mediates HBV viremia in SCID>BNX chimeric mice transplanted with human tissue. PCR amplification products of HBV pre-core/core region following DNA extraction from sera of mice, 16 and 31 days after sub-capsular kidney transplantation of normal human liver fragments. The human liver fragments were incubated ex-vivo prior to transplantation with human HBV positive serum (FIG. 2A); HBV serum and hIL6 simultaneously (FIG. 2B), or preincubated with hIL6 and later with HBV sera FIG. 2C). In each of FIGS. 2A to 2C, the upper panel is an EtBr staining and the lower panel is an $^{32}$P HBV linear insert hybridization result of the same gel. The molecular marker size (m) is indicated by an arrow; numbers at the head of each panel indicate mice identification numbers; + for positive serum control and – for negative serum control.

FIG. 2D shows HBsAg staining of an ex-vivo HBV incubation of a normal liver fragment with hIL6. one month following implantation under the kidney capsule of SCID>BNX mice.

Sera from HBV-positive patients, containing approximately $10^8$ virions/ml, were used for infection. Small fragments of normal human liver were incubated with 400 µl sera in 1 ml DMEM supplemented with 2 µg/ml polybrene in the absence (group A) or presence (group B) of hIL6 (500 ng/ml) incubated for 2–4 h at 37° C. In group C, the liver fragments were treated with hIL6 for 2 h at 37° C. before the addition of HBV-positive sera and polybrene. After incubation, 4–5 ml polybrene DMEM were added and the liver fragments were transplanted under the kidney capsule to groups A, B and C of SCID>BNX chimeric mice (10, 19 and 11 mice, respectively). At 2 weekly intervals for 4 months, blood was collected retrobulbarily from each mouse. 100 µl of serum samples were treated with 0.5 mg/ml proteinase K in 10 mM EDTA and 0.25% SDS for 2 h at 55° C. or overnight at 37° C., extracted twice with phenol, once with phenol-CHCl$_3$, and once with CHCl$_3$. DNA was precipitated with ethanol, using 0.5M NaCl and a DNA microcarrier. DNA was dissolved in 30 µl Tris-EDTA, pH 8.0, and was subjected to PCR amplification.

The 50 µl PCR reaction volume contained 10 pmole of each oligonucleotide primer in reaction buffer (10 mM Tris-HCl, pH 8.3, 50 mM KCl, 2.0 mM MgCl$_2$, 0.01% (w/v) gelatin, 250 µM of dATP, dGTP, dCTP, dTTP and 0.5 u of Taq polymerase. The reaction mixtures were overlaid with 30 µl of mineral oil. PCR cycles included 94° C. for 1 min., 55° C. for 1 min. and 72° C. for 3 min., 35 repeated cycles. 10 µl of reaction mixture was analyzed on a 2% agarose gel. Oligonucleotides used for the pre-core/core amplification were:

oligo 1, Sense (nt 1778 to 1806):
5' GGA-GGC-TGT-AGG-CAT-AAA-TTG-GTC-TGC-GC-3'. Sequence ID No. 7
oligo 2, Antisense (nt 2446 to 2408):
5' CCC-GAG-ATT-GAG-ATC-TTC-TGC-GAC-GCG-GCG-ATT-GAG-ACC-3'. Sequence ID No. 8

Sequence originated from adw subtype; nt numbering starts from EcoRI site. The expected size of the PCR DNA product is 668-bp.

The PCR samples were electrophoresed on 2% agarose gel and transferred to a nylon membrane (Biodynea), hybridized with a nick-translated probe. The autoradiogram was exposed with intensifying screens at –70° C. for 7 h. In order to confirm the PCR results, the mice serum samples were also subjected to PCR amplification with primers spanning the envelope gene region, showing the same results (data not shown).

Reproducible results were obtained from four similar experiments while there were 10–20 mice in each group.

Based on the present discovery that hIL6 acts to mediate HBV infection, it is possible to prepare an antiviral/anti-HBV agent. A pharmaceutical composition for the prevention of HBV infection, comprising an active ingredient having an amino acid sequence similar to hIL6, is thus developed. The hIL6 domain which interacts with hIL6Rα (R for receptor) and/or hiL6Rβ (amino acid residues: 40–60, 70–100 and 135–175) antagonizes hIL6 interaction to prevent HBV infection.

Set forth at FIG. 4 is the nucleotide sequence for human interleukin 6 mRNA (SEQ ID NO 1), as published by L. T. May, et al., "Anti-beta Interferon Antibodies Inhibit the Increased Expression of HLA-B7 mRNA in Tunor Necrosis Factor-Treated Human Fibroblasts: Structural Studies of the beta-2 Interferon Involved," Proc. Nat'l Acad. Sci. U.S.A. 83 (23), 8957–8960 (1986).

FIGS. 5*a* and 5*b* depict the nucleotide sequence for the human interleukin 6 receptor mRNA (SEQ ID NO 2), as published by K. Yamasuki, et al., "Cloning and Expression of the Human Interleukin 6 (BSF-2/ISN beta 2) Receptor," Science 241 (4867), 825–828 (1988).

FIG. 6 depicts the nucleotide sequence for the interleukin-6 receptor (SEQ ID NO 3), as published by H. Schooltink, et al., "Structural and Functional Studies on the Human Nepatic Interleukin-6 Receptor," Biochem. J. 277:659–664 (1991).

FIGS. 7*a* and 7*b* depict the nucleotide sequence for the gp 130 interleukin 6 receptor (SEQ ID NO 4), as published by M. Hibi, et al, "Molecular Cloning and Expression of an IL-6 Signal Transducer, gp 130," Cell 63 (6), 1149–1157 (1990).

FIG. 8 depicts the amino acid sequence for the human interleukin 6 receptor alpha (IL-6R alpha) (SEQ ID NO 5), as published by K. Yamasaki, et al., "Cloning and Expression of the Human Interleukin 6 (BSF-2/ISN beta 2) Receptor," Science 241 (4867), 825–828 (1988).

FIG. 9 depicts the amino acid sequence for human interleukin 6 (SEQ ID No. 6), as published by C. Nishimura, et al., Biochemistry 35:273–281 (1996).

The molecular analysis of hIL6 binding sites with gp130 and gp80 revealed a number of structural targets on hIL6 which can serve as hIL6 antagonists. The preferable target for an hIL6 antagonist is to disrupt the hIL6/hIL6Rα complex with hIL6Rβ.

Based on previous publication, a number of domains essential for hIL6 activity were reported:

1. Lys41-ala56 (site 2a, also named β2) is involved in the activation of signal-transduction.
2. Gly77-glu95 (site 2c) is important for interaction with hIL6Rα, subunit gp80.
3 Gln153-his165 (site β1), substitution of trp158 to arg or gln160 to glu combined with thr163 to pro-antagonize the biological activity of hIL6.
4. A combined β1 and β2 hIL6 mutant (mhIL6β1+β2) is inactive on XG-1 hIL6 responsive cells, with a weakly antagonizing activity.
5. The addition of two substitutions to the mhIL6 (m for mutant) β1+β2, phe171 to leu and ser177 to arg, resulted in an increase in the affinity to hIL6Rα, while inhibiting its activity on XG-1 cells.

Based on techniques known per se to persons skilled in the art, the proteins and peptides for use in the pharmaceutical compositions of the present invention are readily prepared, e.g., by the following techniques and steps:

Amplification of chosen segment of DNA from plasmid containing HBV DNA (adw2)-adw HTD by PCR, using primers constructed so as to introduce BamH1 and EcoR1 sites compatible to the pGEX-2T (Pharmacia, Uppsala, Sweden, Catalogue No. 27-4801-01) insertion site. This GST fusion vector provides a system in which fusion proteins are easily purified from the bacterial lysates and can be detected directly as a fusion protein or after cleavage with site specific proteases. After introduction of DNA into pGEX-2T, competent *E. coli* (JM109) are transformed and cloned (LB+10 μg/ml ampicillin). Protein expression is induced by the addition of IPTG (0.1 mM, isopropyl-1-thio-b-D-galactoside) for 1–2 hours. Fusion protein is removed from lysed (sonicated) cells by collection on glutathione-agarose beads (Pharmacia) and eluted from beads using reduced glutathione (5 mM in 50 mM Tris-Cl, pH 8.0). Identification and determination of protein can be done either by use of antibodies to GST or by specific recognition of inserted protein. The complete HBV pS1 protein (aa 1 to aa 119, applying PCR with the sense and anti-sense primers 5'-CGGGATCCATGGGAGGTTGGTCATC-3'[NT 8+2856–2873, EcoR1 as starting site for nt numbering] (Sequence ID No. 9) and 5'-GGAATTCCACTGCATGGC-3' [nt 6-3210] respectively) (Sequence ID No. 10) and the pS1 attachment site aa21 to aa46 constructs were designed and produced in the pGEX-2T system (compound B in FIG. 1).

Truncated soluble forms of gp80 and gp130 are synthesized using the pGEX-2T system as described for the preparation of pS1 (compound A2 and A1, respectively). hIL6 derived peptides (Lys41-ala56, Gly77-glu95 and Gln153-his165, designated C1, C3 and C2, respectively, in FIG. 1) are synthesized by applying a variety of methods including Merrifield solid-phase synthesis and derived methods or other acceptable genetic engineered methods. The compounds produced are linear or cyclic peptides, or parts of large proteins.

Compositions according to the present invention can be administered orally or parenterally, including intravenous, intraperitoneal, intranasal and subcutaneous administration. Implants of the compounds are also useful.

The proteins of the present invention are administered in combination with other drugs, or singly, consistent with good medical practice. The composition is administered and dosed in accordance with good medical practice, taking into account the clinical condition of the individual patient, the site and method of administration, scheduling of administration, and other factors known to medical practitioners. The 'effective amount' for purposes herein is thus determined by such considerations as are known in the art.

When administering the compositions parenterally, the pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin by the maintenance of the required particle size in the case of dispersion, and by the use of surfactants. Non-aqueous vehicles such as cottonseed oil, sesame oil, olive oil, soybean oil, corn oil, sunflower oil, or peanut oil and esters such as isopropyl myristate, may also be used as solvent systems for compound compositions. Additionally, various additives which enhance the stability, sterility, and isotonicity of the compositions, including antimicrobial preservatives, anti-oxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example sugars, sodium chloride, and the like. Prolonged absorption of the injectable pharmaceutical form can be brought about by the use of agents delaying absorption, for example, aluminum monostearate and gelatin. According to the present invention, however, any vehicle, diluent or additive used would have to be compatible with the compounds.

Sterile injectable solutions can be prepared by incorporating the proteins utilized in practicing the present invention in the required amount of the appropriate solvent with various of the other ingredients, as desired.

A pharmacological formulation described and claimed herein can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems, such as polymer matrices, liposomes, and microspheres. An implant suitable for use in the present invention can take the form of a pellet which slowly dissolves after being implanted, or a biocompatible delivery module well-known to those skilled in the art. Such well-known dosage forms and modules are designed such that the active ingredients are slowly released over a period of several days to several weeks.

Examples of well-known implants and modules useful in the present invention include: U.S. Pat. No. 4,487,603, which discloses an implantable micro-infusion pump for dispensing medication at a controlled rate; U.S. Pat. No. 4,486,194. which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow, implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems and modules are well-known to those skilled in the art.

A pharmacological formulation of the present invention can be administered orally to the patient. Conventional methods such as administering the compounds in tablets, suspensions, solutions, emulsions, capsules, powders, syrups and the like, are usable. Known techniques which deliver the new compositions orally or intravenously and retain the biological activity, are preferred.

In one embodiment, the new compositions can be administered initially by intravenous injection. The quantity of the compositions to be administered will vary for the patient being treated, and will vary from about 100 ng/kg of body weight to 100 mg/kg of body weight per day, and preferably will be from 10 µg/kg to 10 mg/kg per day.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A method for inhibiting the infection of hepatocytes by HBV, comprising administering to a human patient a soluble active agent which inhibits the interaction between human interleukin 6 (hIL6) and hepatocytes, and thereby inhibits the activation of gp130 and the internalization of HBV into the hepatocytes, said soluble active agent selected from the group consisting of glycoprotein 80 (gp80) having receptor sites which interact with hIL6, soluble glycoprotein 130 (gp130) having receptor sites which interact with hIL6, hIL6 derived petide LYS41-ALA56, hIL6 derived peptide GLY77-GLU95, hIL6 derived peptide GLN153-HIS165, a combined β1 and β2 hIL6 mutant (mhIL6β1+β2), mhIL6β1+β2 substituted with phe 171 to leu and ser 177 to arg, a soluble active agent which disrupts the hIL6/hIl6Rα complex with hIL6Rβ, and mixtures of any of the foregoing.

2. The method of claim 1, wherein said active agent competitively interacts with at least one of the binding sites.

3. The method of claim 2, wherein said soluble active agent comprises a soluble glycoprotein 80 (gp80) and/or soluble glycoprotein 130 (gp130) having receptor sites which bind to hIL6 and competitively inhibit the interaction between hIL6 and hepatocytes.

4. The method of claim 2, wherein said soluble active agent comprises a soluble ligand selected from the group consisting of peptides LYS41-ALA56, GLY77-GLU95 and GLN153-HIS165 and competitively blocks the interaction of hIL6 with hepatocytes.

5. The method of claim 2, wherein said soluble active agent disrupts the hIL6/hIl6Rα complex with hIL6Rβ.

6. The method of claim 2, wherein said soluble active agent is selected from the group consisting of hIL6 derived peptide LYS41-ALA56, hIL6 derived peptide GLY77-GLU95, hIL6 derived peptide GLN153-HIS165, a combined β1 and β2 hIL6 mutant (mhIL6β1+β2), and mhIL6β1+β2 substituted with phe 171 to leu and ser 177 to arg, and mixtures of any of the foregoing.

7. The method of claim 1, wherein said soluble active agent is administered in an amount from about 100 ng/kg to about 100 mg/kg per day, based on the body weight of the patient.

8. The method of claim 7, wherein said soluble active agent is administered in an amount from about 10 µg/kg to about 10 mg/kg, based on the body weight of the patient.

9. The method of claim 1, wherein the soluble active agent is administered orally to the patient.

10. The method of claim 1, wherein the soluble active agent is administered parenterally to the patient.

11. The method of claim 1, wherein the soluble active agent is implanted into the patient.

* * * * *